(12) United States Patent
Lee et al.

(10) Patent No.: US 7,501,222 B2
(45) Date of Patent: Mar. 10, 2009

(54) PHOTORESIST MONOMER POLYMER THEREOF AND PHOTORESIST COMPOSITION INCLUDING THE SAME

(75) Inventors: Jung-Youl Lee, Kyungki-Do (KR); Jae-Woo Lee, Kyungki-Do (KR); Jae-Hyun Kim, Kyungki-Do (KR)

(73) Assignee: Dongjin Semichem Co., Ltd. (KR)

( * ) Notice: Subject to any disclaimer, the term of this patent is extended or adjusted under 35 U.S.C. 154(b) by 226 days.

(21) Appl. No.: 11/471,838

(22) Filed: Jun. 21, 2006

(65) Prior Publication Data

US 2006/0292489 A1    Dec. 28, 2006

(30) Foreign Application Priority Data

Jun. 24, 2005   (KR) .................. 10-2005-0055190
Aug. 12, 2005  (KR) .................. 10-2005-0074435

(51) Int. Cl.
G03C 1/73 (2006.01)
G03F 7/039 (2006.01)
G03F 7/20 (2006.01)
G03F 7/30 (2006.01)

(52) U.S. Cl. ................ 430/270.1; 430/910; 430/905; 430/914; 430/921; 430/925; 430/325; 430/326; 526/282; 526/284; 526/308; 526/309; 526/328; 526/328.5; 526/329.7; 560/116; 560/117; 560/118; 560/119; 560/120; 560/121; 560/354

(58) Field of Classification Search .............. None
See application file for complete search history.

(56) References Cited

U.S. PATENT DOCUMENTS 4,975,519 A    12/1990  Yang et al. ............... 528/230
6,569,602 B1 *  5/2003  Wang ..................... 430/281.1
2002/0143130 A1  10/2002  Lee et al. ................ 526/266

* cited by examiner

*Primary Examiner*—Sin J. Lee
(74) *Attorney, Agent, or Firm*—Park & Associates IP Law LLC

(57) ABSTRACT

A polymer including a monomer represented by the following Formula and a photoresist composition including the same are disclosed. The polymer and photoresist composition can improve the resolution and the process margin due to the low activation energy of the deprotection reaction of the alcohol ester group including saturated cyclic hydrocarbyl group, and also can produce fine photoresist patterns because they have a stable PEB(Post Exposure Baking) temperature sensitivity, and further, can improve the focus depth margin and the line edge roughness of the resist layer.

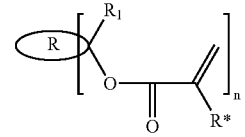

In the above Formula, R* is a hydrogen or methyl group, $R_1$ is saturated hydrocarbyl group of 1 to 5 carbon atoms, R is mono-cyclic or multi-cyclic homo or hetero saturated hydrocarbyl group of 3 to 50 carbon atoms, and n is an integer of at least 2.

15 Claims, 3 Drawing Sheets

PHOTORESIST MONOMER POLYMER THEREOF AND PHOTORESIST COMPOSITION INCLUDING THE SAME

CROSS-REFERENCE TO RELATED APPLICATIONS

This application claims priorities of Korean Patent Application Nos. 10-2005-0055190 filed on Jun. 24, 2005 and 10-2005-0074435 filed on Aug. 12, 2005.

FIELD OF THE INVENTION

This invention relates to a photoresist composition, and more particularly, to a photoresist monomer, a polymer thereof and a photoresist composition including the same, which can improve the resolution of a photolithography process, the process margin, and so on, because of the low activation energy of the deprotection reaction of the alcohol ester having saturated cyclic hydrocarbyl group.

BACKGROUNDS OF THE INVENTION

Recently, as the integration degree and the precision of semiconductor devices increase, the formation of ultra-fine photoresist patterns, which have a half pitch of less than 90 nm, is needed in the photolithography process for producing the semiconductor devices. Consequently, the wavelength of an exposure light is reduced to less than 193 nm in the photolithography process, and various technologies for optimizing the pattern forming process have been being developed. In order to form the fine photoresist patterns, it is also necessary to develop photosensitive materials having a low LER(Line Edge Roughness), a law PEB(Post Exposure Baking) temperature sensitivity, and a good dry etching resistance.

In order to improve the resolution and the process margin in the process for forming the photoresist pattern, and to produce a more fine photoresist pattern, the photosensitive photoresist polymer should have a low activation energy in the deprotection reaction of the protecting group, in which the protecting group is adhered to the chain of the photoresist polymer for inhibiting the dissolution of the polymer against a basic solution. For example, the photoresist polymer which can be used for ArF exposure light source include polyacrylate, cycloolefin-maleic anhydride copolymer, polynorbornene and so on, and they are classified into (i) a polymer having the high activation energy protecting group, such as a tertiary butyl group, (ii) a polymer having the medium activation energy protecting group, such as methyl adamantly group or an ethyl adamantly group, and (iii) a polymer having the low activation energy protecting group, such as an acetal group or ketal nobornene group, according to the magnitude of the activation energy of the deprotection reaction of the protecting group which is adhered to the chain of the polymer.

As the photoresist polymer for ArF exposure light source, poly(meth)acrylate having acetal groups, which belong to the low activation energy protecting group, is disclosed in U.S. Pat. No. 4,975,519, U.S. Patent Publication No. 2002-0143130(2002.10.03), and so on. However, it is not disclosed a monomer which have at least 2 (meth)acrylates, particulary, a (meth)acrylate monomer and polymer, which have at least 2 crosslinking alcohol esters as a protecting group for inhibiting the dissolution of the polymer against a basic solution.

SUMMARY OF THE INVENTION

Therefore, it is an object of the present invention to provide a photoresist monomer having alcohol ester groups, a polymer thereof and a photoresist composition including the same, which can improve the resolution of the photolithography process, and the process margin due to the low activation energy of the deprotection reaction of the alcohol ester groups, and which can produce fine photoresist patterns due to the low PEB(Post Exposure Baking) temperature sensitivity.

It is other object of the present invention to provide a photoresist monomer having alcohol ester groups, a polymer thereof and a photoresist composition including the same, which can improve the focus depth margin and the line edge roughness of the photoresist patterns.

It is another object of the present invention to provide methods of producing the monomer and the polymer thereof, and a method of forming the photoresist pattern using the photoresist composition.

To accomplish these objects, the present invention provides a monomer represented by the following Formula 1.

[Formula 1]

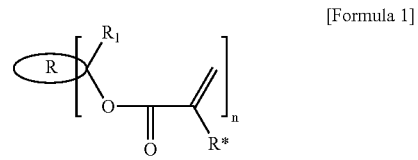

In Formula 1, R* is a hydrogen or methyl group, $R_1$ is saturated hydrocarbyl group of 1 to 5 carbon atoms, R is mono-cyclic or multi-cyclic homo or hetero saturated hydrocarbyl group of 3 to 50 carbon atoms, and n is an integer of at least 2.

The present invention also provides a photoresist polymer including a repeating unit represented by the following Formula 2.

[Formula 2]

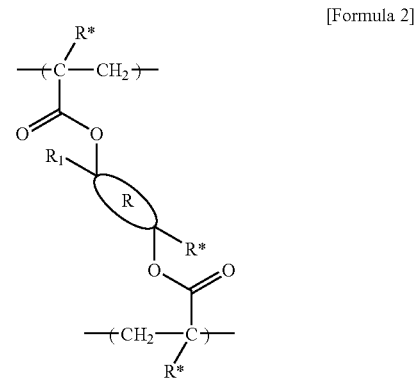

In Formula 2, R*, $R_1$, and R are as defined in Formula 1.

The present invention also provides a photoresist polymer including a repeating unit represented by the following Formula 4.

[Formula 4]

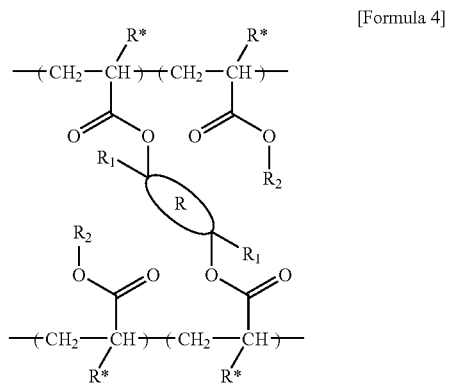

In Formula 4, R* is a hydrogen or methyl group, $R_1$ is saturated hydrocarbyl group of 1 to 5 carbon atoms, $R_2$ is a chain type or ring type alkyl group of 1 to 20 carbon atoms, and R is mono-cyclic or multi-cyclic homo or hetero saturated hydrocarbyl group of 3 to 50 carbon atoms.

The present invention also provides a photoresist composition including the polymer and a method of forming the photoresist pattern using the photoresist composition.

DETAILED DESCRIPTION OF THE INVENTION

Figure 1:
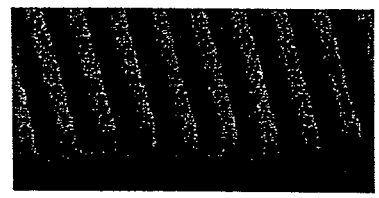
FIGS. 1 to 14 are SEM (Scanning Electron Microscopy) photographs of photoresist patterns which were formed with the photoresist compositions according to the examples of the present invention.

A more complete appreciation of the invention, and many of the attendant advantages thereof, will be better appreciated by reference to the following detailed description.

The photoresist monomer having alcohol ester groups and a cyclic hydrocarbyl group according to the present invention can be represented by the following Formula 1.

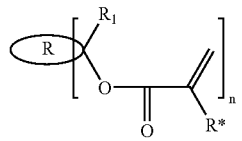

[Formula 1]

In Formula 1, R* is a hydrogen or methyl group, $R_1$ is saturated hydrocarbyl group of 1 to 5 carbon atoms, R is mono-cyclic or multi-cyclic homo or hetero saturated hydrocarbyl group of 3 to 50 carbon atoms, and preferably, R is selected from the group consisting of

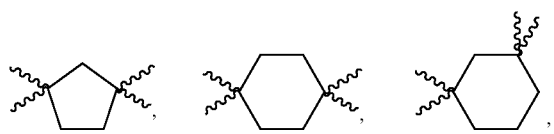

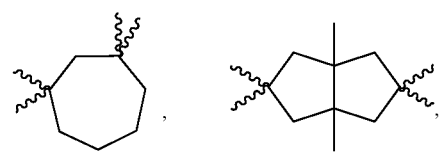

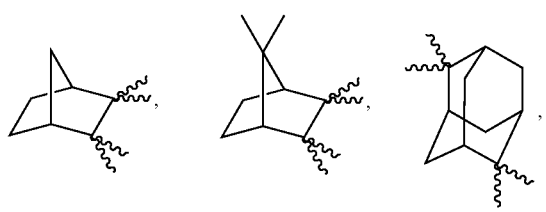

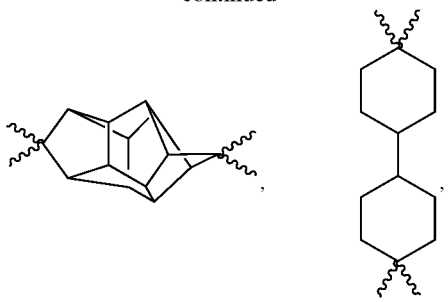

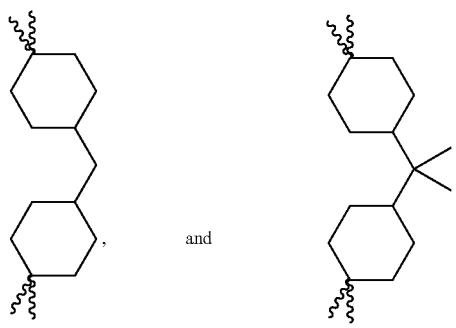

-continued

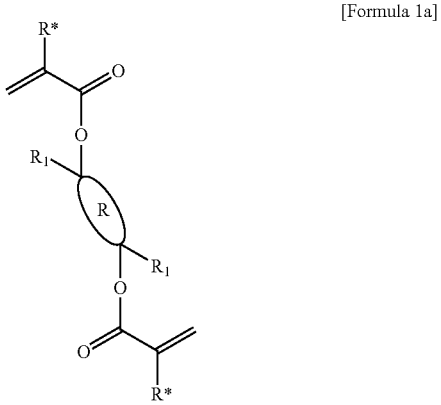

And n is an integer of at least 2, and preferably is from 2 to 4.

The following Formula 1a is an example of Formula 1 when n is 2.

[Formula 1a]

In Formula 1a, R*, $R_1$, and R are as defined in Formula 1.

The monomer having alcohol esters and a saturated cyclic hydrocarbyl group, which is represented by Formula 1 according to the present invention, can be prepared by the reaction of (meth)acryloyl chloride and cyclic diol in the presence of a basic catalyst. The cyclic diol can be prepared by the reaction of alkylmagnesium and cyclic ketone having at least 2 ketone groups. For example, as shown in Reaction 1a, the cyclic diol can be prepared by the reaction of a cyclic ketone and alkyl magnesium bromide ($R_1$MgBr), wherein $R_1$ is an alkyl group of 1 to 5 carbon atoms.

[Reaction 1a]

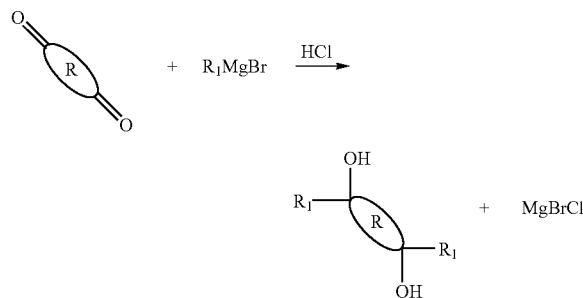

In Reaction 1a, $R_1$ and R are as defined in Formula 1.

The reaction can be carried out by preparing cyclic ketone having at least 2 ketone groups under inert atmosphere, such as nitrogen or argon atmosphere, and then dropping alkyl magnesium bromide at the temperature of −78 to 20° C. and at room pressure, for 1 to 12 hours, in a conventional organic solvent, such as tetrahydrofuran(THF). Then, as shown in Reaction 1b, the monomer represented by Formula 1 can be prepared by the reaction of the obtained cyclic diol and (meth) acryloyl chloride in the presence of a basic catalyst.

[Reaction 1b]

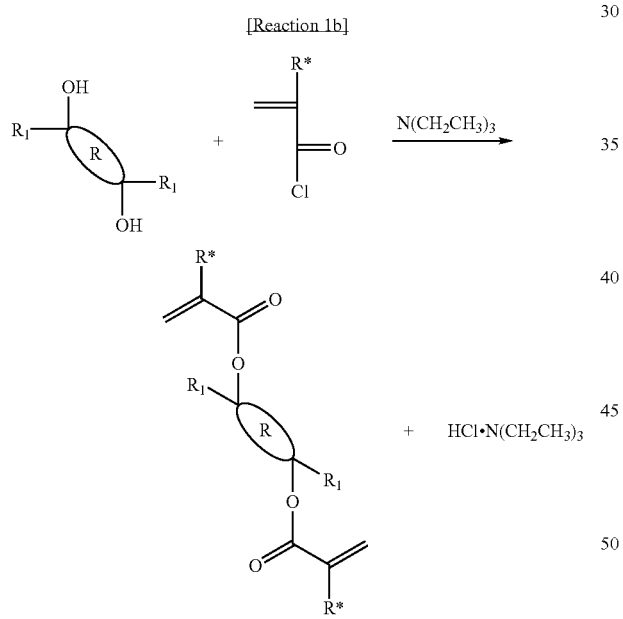

In Reaction 1b, $R^*$, $R_1$ and R are as defined in Formula 1.

As the basic catalyst, conventional various basic catalysts can be used, and the representative example of the basic catalyst is triethylamine. The reaction can be carried out under inert atmosphere including nitrogen or argon, and so on, at the temperature of 0 to 60° C. and at room pressure, for 1 to 24 hours, in the conventional organic solvent, such as tetrahydrofuran(THF).

Alternatively, the monomer having alcohol esters including a saturated cyclic hydrocarbyl group, which is represented by Formula 1 according to the present invention, can be simply prepared by the one-step reaction of (meth)acryloyl chloride, alkylmagnesium and a cyclic ketone having at least 2 ketone groups.

[Reaction 2]

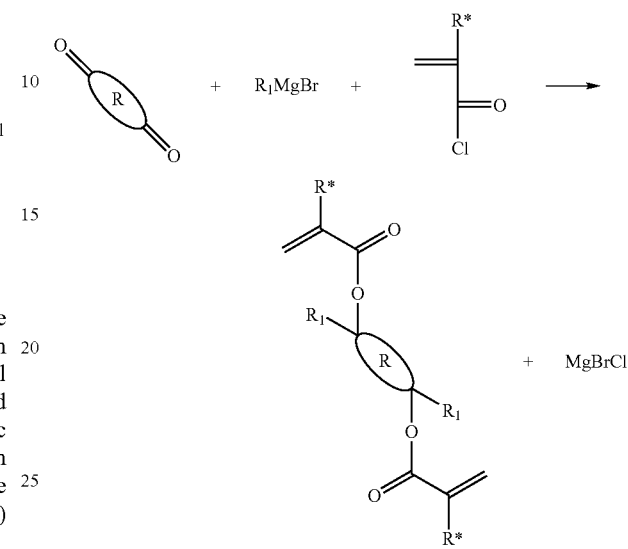

In Reaction 2, $R^*$, $R_1$ and R are as defined in Formula 1.

Particularly, the reaction can be carried out by preparing cyclic ketone having at least 2 ketone groups under nitrogen or argon atmosphere, and then dropping alkyl magnesium bromide at the temperature of −78 to 20° C. and at room pressure, for 1 to 12 hours, in a conventional organic solvent, such as tetrahydrofuran(THF). Successively, the monomer represented by Formula 1 can be prepared by dropping (meth) acryloyl chloride at the temperature of −20 to 60° C.

The photoresist polymer having alcohol ester groups according to the present invention includes a repeating unit represented by the following Formula 2.

[Formula 2]

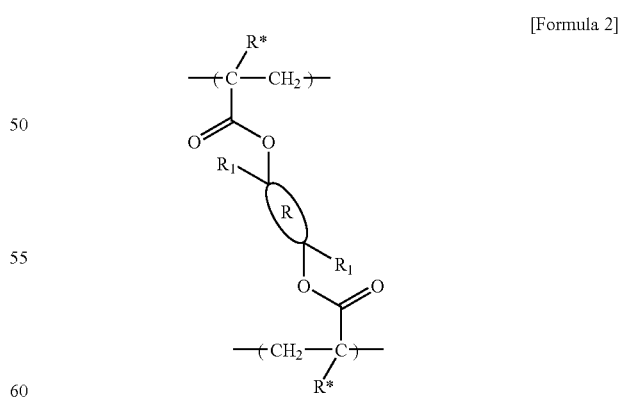

In Formula 2, R, $R^*$, and $R_1$ are as defined in Formula 1.

The preferable photoresist polymer having alcohol ester groups according to the present invention can be represented by the following Formula 3, and the more preferable polymer can be represented by the Formulas 3a to 3g.

[Formula 3]

[Formula 3a]

[Formula 3b]

[Formula 3c]

[Formula 3d]

[Formula 3e]

-continued

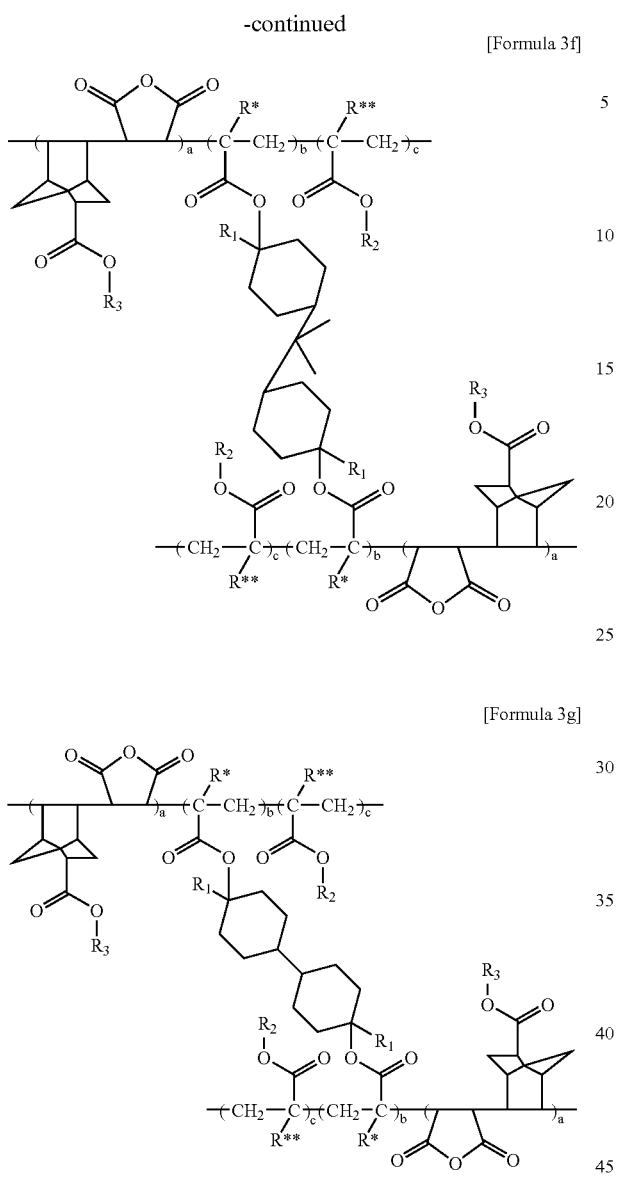

[Formula 3f]

[Formula 3g]

In Formulas 3 and 3a to 3g, R*, R** are independently a hydrogen or methyl group, $R_1$ is saturated hydrocarbyl group of 1 to 5 carbon atoms, $R_2$, $R_3$ are chain type or ring type alkyl group of 1 to 20 carbon atoms, R is mono-cyclic or multi-cyclic homo or hetero saturated hydrocarbyl group, a, b and c are mole % of the repeating units in the upper and lower polymer chains, and are respectively 1~95 mole %, 1~95 mole % and 1~95 mole %, and preferably 2.5~95 mole %, 2.5~95 mole % and 2.5~95 mole % in the upper or lower polymer chain.

In addition, the photoresist polymer according to the present invention may include a repeating unit represented by the following Formula 4, which is formed by bonding (meth)acrylate crosslinking monomer having alcohol ester groups and (meth)acrylate monomer having chain type or ring type alkyl group.

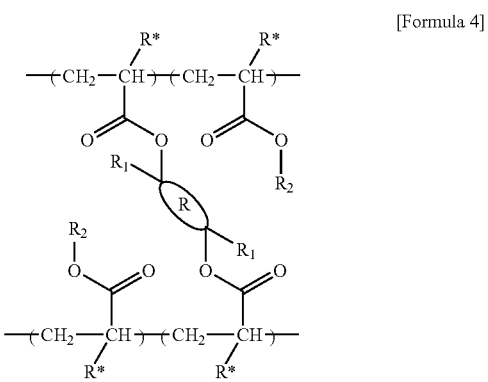

[Formula 4]

In Formula 4, R, R*, and $R_1$ are as defined in Formula 1, and $R_2$ is chain type or ring type alkyl group of 1 to 20 carbon atoms.

The preferable photoresist polymer having alcohol ester groups according to the present invention can be represented by the following Formula 5, and the more preferable polymers can be represented by the Formulas 5a to 5g.

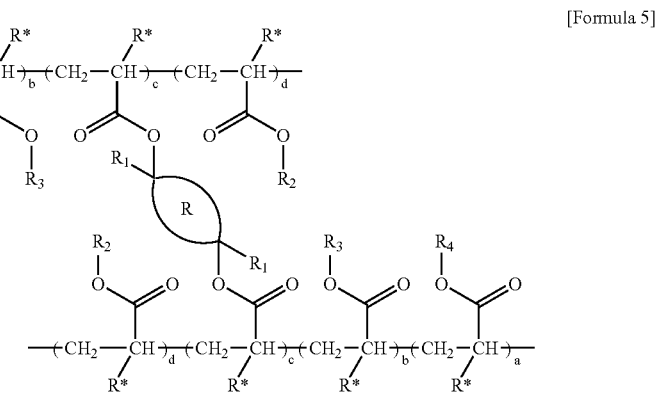

[Formula 5]

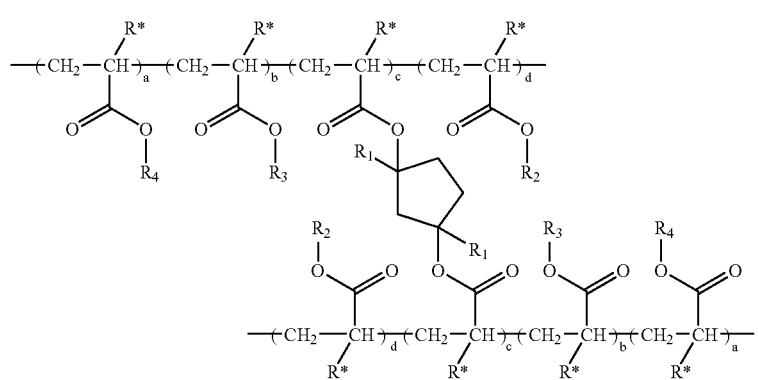
[Formula 5a]
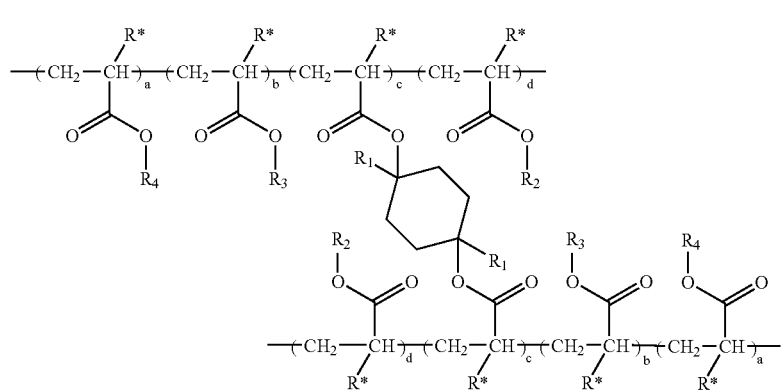
[Formula 5b]
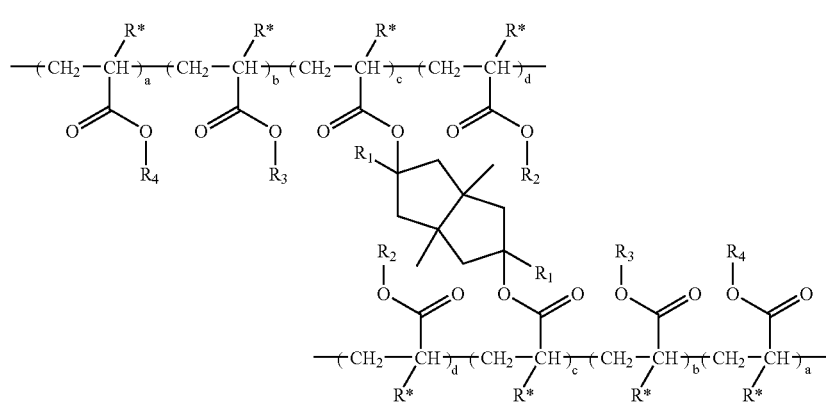
[Formula 5c]
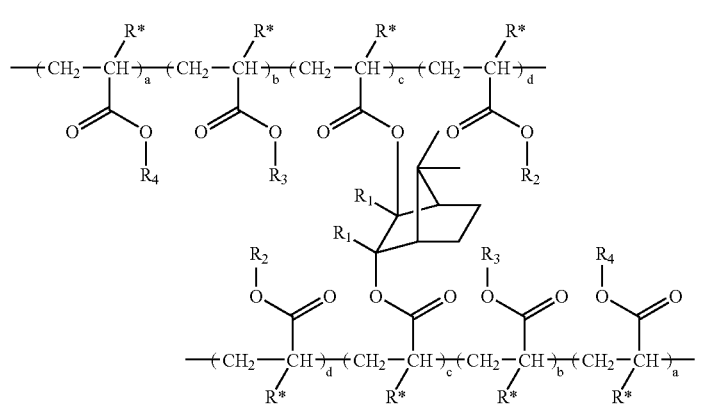
[Formula 5d]

-continued
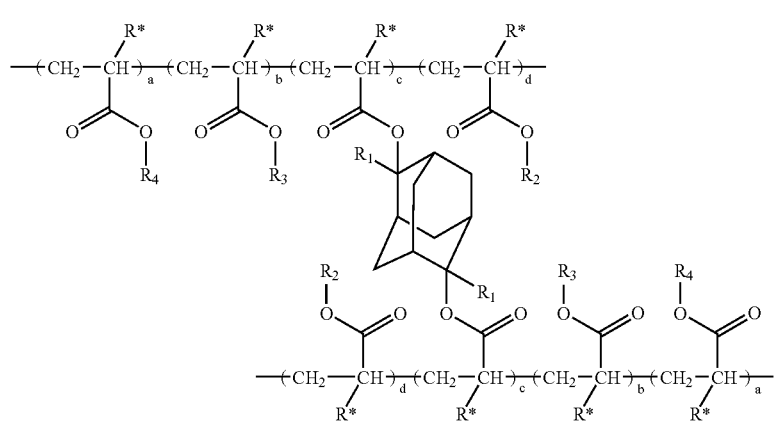
[Formula 5e]
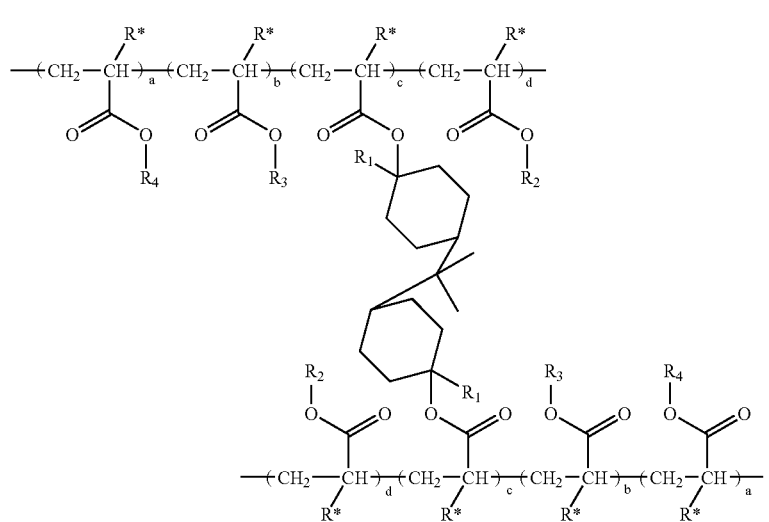
[Formula 5f]
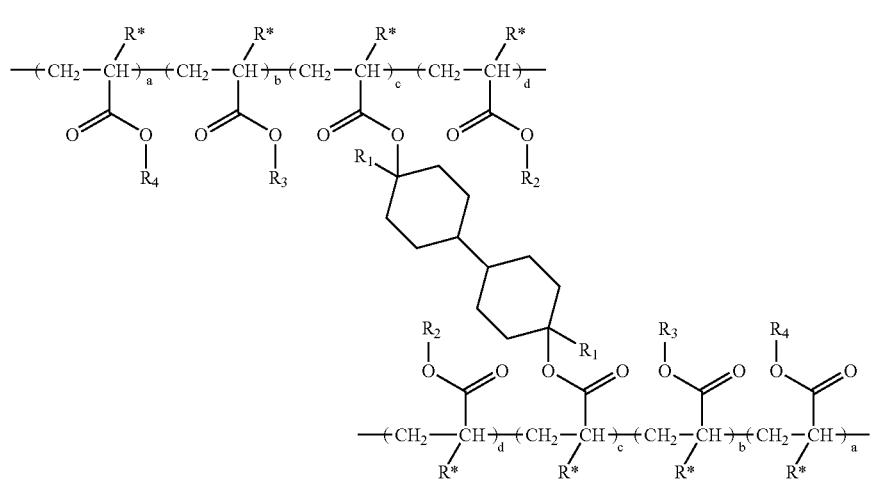
[Formula 5g]

In Formula 5 and 5a to 5g, R* is independently a hydrogen or methyl group, $R_1$ is saturated hydrocarbyl group of 1 to 5 carbon atoms, $R_2$, $R_3$ and $R_4$ are independently chain type or ring type alkyl group of 1 to 20 carbon atoms, R is monocyclic or multi-cyclic homo or hetero saturated hydrocarbyl group of 3 to 50 carbon atoms, and a, b, c and d are mole % of the repeating units in the upper and lower polymer chains, and are respectively 1~95 mole %, 1~95 mole % and 1~95 mole %, preferably 1.67~95 mole %, 1.67~95 mole % and 1.67~95 mole % in the upper or lower polymer chain.

The alcohol ester group, which includes a saturated cyclic hydrocarbyl group and is adhered to the chain of polymer, is a protecting group for preventing the polymer and a photoresist composition including the same from being dissolved by a basic solution, such as a basic developing solution. The protecting group is deprotected by an acid catalyst($H^+$) which is produced from a photo-acid generators when exposed to an exposure light. Then, the solubility of the exposed region increases, and the contrast of the photoresist composition is effectively improved. Especially, the alcohol ester group can improve the resolution of the resist pattern, and the process margin, such as an energy margin due to its low activation energy of the deprotection reaction. In addition, the alcohol ester group can improve the focus depth margin and the line edge roughness because the product of deprotection reaction is a bulky material of high molecular weight. The photoresist polymer according to the present invention is formed only by (meth)acrylate linkages, and thus, the next etching process can be performed even if the coating thickness of the polymer is low, for example is less than 2000 Å. Therefore, the polymer can be used in the lithography process using an extreme short wavelength light source and an electron beam, and the polymerization yield highly increases compared with the conventional hybrid-type polymer. And also, the selectivity of the light exposed area to the light non-exposed area can be improved due to the partially crosslinked structure.

The photoresist polymer including the repeating unit of Formula 2 or 4 can be prepared by the conventional polymerization reaction, for example, by the steps of (a) dissolving (meth)acrylate crosslinking monomer having alcohol ester groups, 1 to 5 kinds of (meth)acrylate monomers having a chain type or ring type alkyl group and a polymerization initiator in a polymerization solvent, and (b) reacting the reaction solution under the inert atmosphere of nitrogen, argon, and so on, at the temperature of 60 to 70° C. for 4 to 72 hours. The polymerization reaction can be carried out by a radical polymerization reaction, a solution polymerization reaction using a metal catalyst. The polymerization method may further include the step of crystallizing and purifying the reaction product with diethyl ether, petroleum ether, a lower alcohol, such as methanol, ethanol or isopropanol, water, mixtures thereof, or so on.

As shown in the following Reaction 3, the photoresist polymer represented by Formula 3 can be prepared by the reaction of Formulas 1a, 1b, 1c and maleic anhydride.

[Formula 1b]

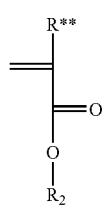

In Formula 1b, R** and $R_2$ are as defined in Formula 3.

[Formula 1c]

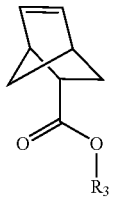

In Formula 1c, $R_3$ is as defined in Formula 3.

[Reaction 3]

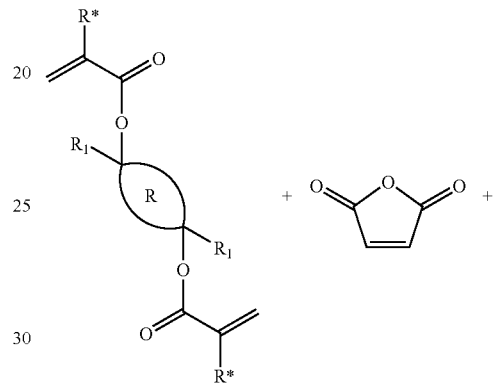

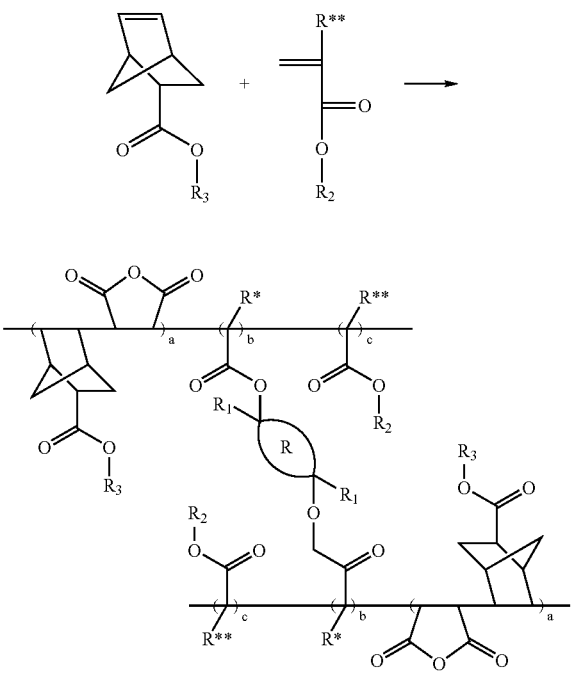

In Reaction 3, R*, R**, $R_1$, $R_2$, $R_3$, R, a, b and c are as defined in Formula 3.

As shown in the following Reaction 4, the photoresist polymer represented by Formula 5 can be prepared by the polymerization reaction of the monomer of Formula 1a and (meth)acrylate monomers having chain type or ring type alkyl group.

[Reaction 4]

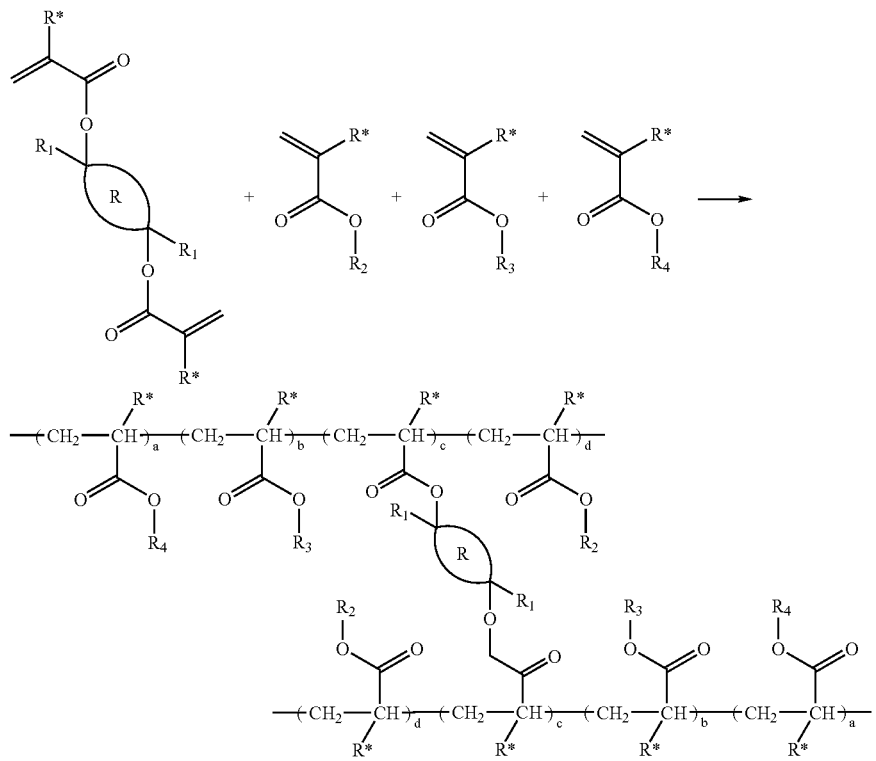

In Reaction 4, R*, R**, $R_1$, $R_2$, $R_3$, R, a, b, c and d are as defined in Formula 5.

As the polymerization solvent, conventional various polymerization solvents for producing a photoresist polymer can be used. Exemplary polymerization solvents includes, but are not limited to, cyclohexanone, cyclopentanone, tetrahydrofuran, dimethylformaide, dimethylsulfoxide, dioxane, methylethylketone, benzene, toluene, xylene, and the mixtures thereof. Polymerization initiator also can be selected from conventional various polymerization initiators. Exemplary polymerization initiators include benzoylperoxide, 2,2'-azo-bisisobutyronitirile(AIBN), acetylperoxide, lauryl peroxide, t-butyl peracetate, t-butyl hydroperoxide, di-t-butyl peroxide, and the mixtures thereof, which are well known to those skilled in the art. The preferable weight average molecular weight(Mw) of the photosensitive polymers of Formula 3 or 5 is from 3,000 to 100,000, and the preferable polydispersity (PD) of the polymers is from 1.0 to 5.0. If the weight average molecular weight(Mw) and the polydispersity(PD) of the polymers are out of the range, the property of photoresist layer and the contrast of patterns can be deteriorated or the photoresist layer cannot be formed.

The photoresist composition according to the present invention includes the photosensitive polymer including the repeating unit of Formula 2 or 4, a photo-acid generator for producing an acid component, and an organic solvent. If necessary, the photoresist composition may further include various additives. The preferable amount of photosensitive polymer including the repeating unit of Formula 2 or 4 is 1 to 30 weight %, and more preferably 5 to 15 weight % with respect to the total photoresist composition. If the amount of the photosensitive polymer is less than 1 weight %, the formation of patterns having desired thickness is in trouble, because the resist layer becomes too thin. If the amount of the photosensitive polymer is more than 30 weight %, the uniformity of the coating layer may be deteriorated.

The photo-acid generator produces an acid component such as $H^+$ when exposed to a light source. Therefore, the photo-acid generator deprotects the protection group of the photosensitive polymer. As the photo-acid generator, any compound, which can generate an acid component when exposed to light, can be used. Preferable examples of the photo-acid generator include sulfonium compound such as organic sulfonic acid, onium compound such as onium salt, and the mixtures thereof. The non-limiting examples of the photo-acid generator include phthalimidofluoromethane sulfonate, which has a low light absorbance at 157 nm and 193 nm, dinitrobenzyltosylate, n-decyl disulfone, naphtylimido trifluoromethan sulfonate, diphenyliodonium hexafluorophosphate, diphenyliodonium hexafluoroarsenate, diphenyliodonium hexafluoroantimonate, diphenyl-p-methoxyphenylsulfonium triflate, diphenyl-p-toluenylsulfonium triflate, diphenyl-p-isobutylphenylsulfonium triflate, triphenylsulfonium hexafluoro arsenate, triphenylsulfonium hexafluoro antimonate, triphenylsulfonium triflate, dibutylnaphtylsulfonium triflate, and the mixtures thereof.

The preferable amount of the photo-acid generator is 0.05 to 10 weight % with respect to the total photoresist polymer. If the amount of the photo-acid generator is less than 0.05 weight %, the deprotection of the protection group may be in trouble, because the sensitivity of the photoresist composition against light decreases. If the amount of the photo-acid generator is more than 10 weight %, the profile of the resist patterns may be deteriorated because the photo-acid generator absorbs a lot of ultraviolet rays and a large quantity of acid is produced from the photo-acid generator.

The remaining component of the photoresist composition according to the present invention is the organic solvent. The organic solvent can be selected from the conventional various solvents, which are used for the preparation of a photoresist composition. Exemplary organic solvent include, but are not limited to, ethyleneglycol monomethylether, ethyleneglycol monoethylether, ethyleneglycol monoacetate, diethyleneglycol, diethyleneglycol monoethylether, propyleneglycol monomethyletheracetate, propyleneglycol, propyleneglycol monoacetate, toluene, xylene, methylethylketone, methylisoamylketone, cyclohexanone, dioxane, methyl lactate, ethyl lactate, methylpyruvate, ethylpyruvate, methylmethoxy propionate, ethylethoxy propionate, N,N-dimethylformamide, N,N-dimethylacetamide, N-methyl-2-pyrollidone, 3-ethoxyethylpropionate, 2-heptanone, gamma-butyrolactone, ethyl 2-hydroxypropionate, ethyl 2-hydroxy-2-methyl propionate, ethoxyethyl acetate, hydroxylethyl acetate, methyl 2-hydroxy-3-methylbutanoate, methyl 3-methoxy-2-methylpropionate, ethyl 3-ethoxypropionate, ethyl 3-methoxy-2-methylpropionate, ethyl acetate, butyl acetate, and the mixtures thereof.

If necessary, the photoresist composition may further include organic base compound. Exemplary organic base components include, but not limited to, triethylamine, triisobutylamine, triisooctylamine, diethanolamine, triethanolamine and the mixtures thereof. The preferable amount of the organic base is from 0.01 to 2.00 weight % with respect to the photoresist composition. If the amount of the organic base is less than 0.01 weight %, the undesirable T-top phenomenon may be occurred at the resist pattern. If the amount of the organic base is more than 2.00 weight %, the pattern forming rate may be lowered because the sensitivity of photoresist composition decreases.

The photoresist composition according to the present invention can be prepared by mixing the photosensitive polymer, the photo-acid generator, the organic solvent, and, if necessary, various additives, and by filtering the mixture. Here, the preferable concentration of the solid components in the composition is from 10 to 60 weight %. If the concentration of the solid components is less than 10 weight %, the formation of patterns having a desirable thickness may be in trouble, because the coated resist layer becomes too thin. If the concentration of the solid components is more than 60 weight %, the uniformity of the coating layer may be deteriorated.

In order to form the photoresist pattern with the photoresist composition according to the present invention, the following conventional photolithograph process can be carried out. First, the photoresist composition is applied on a substrate such as silicon wafer, an aluminum substrate, and so on, for example, with a spin coater to form a photoresist layer. Subsequently, the photoresist layer is exposed to a light source to form a predetermined pattern. After the exposure, if necessary, the photoresist pattern is thermally treated, which is referred to as a PEB(Post Exposure Bake) and is developed. The prepared photoresist pattern is used to produce a semiconductor having a predetermined circuit patterns. As the developing solution for the developing process, alkali solution including alkali compounds such as sodium hydroxide, potassium hydroxide, sodium carbonate, tetramethylammonium hydroxide(TMAH) of the concentration of 0.1 to 10 weight % can be used. If necessary, the developing solution may further include water-soluble organic solvent such as methanol, ethanol and surfactant with a proper amount. After carrying out the developing process, the cleaning process of the substrate can be carried out, in which the substrate is washed with purified water.

Hereinafter, the preferable examples are provided for better understanding of the present invention. However, the present invention is not limited to the following examples.

EXAMPLE 1-1

Preparation of Monomer

A. Preparation of Cyclic Diol of Formula 6a

After using 9.8 g(0.1 mol) of cyclopentane-1,3-dione, 100 g of THF into 500 ml 3 necks round-bottom flask, the reaction mixture was cooled to the temperature of −78° C. under nitrogen atmosphere. Thereafter, 66.67 g(0.2 mol) of 3.0M-methyl magnesium bromide was added to the reaction mixture with dropping funnel for 30 minutes. And then, the reaction mixture was heated to room temperature and stirred for 2 hours. After completion of the reaction, 100 ml of water was added to the reaction solution. Thereafter, the reaction solution was placed in a separatory funnel, and extracted with ethylacetate for 3 times. The extract was purified by a column chromatography(hexane:ethylacetate=1:1) to obtain 10.2 g of 1,3-dimethyl-cyclopentane-1,3-diol represented by the following Formula 6a with 78% yield. {$^1$H-NMR(CDCl$_3$): δ(ppm), 3.45(OH, 2H), 1.55(CH$_2$, 2H), 1.40(CH$_2$, 4H), 0.89(CH$_3$, 6H)}

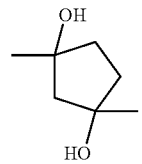

[Formula 6a]

B. Preparation of Monomer of Formula 7a 13.02 g of cyclic diol prepared in Example 1-1-A, which is represented by Formula 6a, was placed in 500 ml 3 necks round-bottom flask, and diluted by 100 g of THF. Then, the reactor was cooled to the temperature of 0° C. A mixture of 18.2 g of acryloyl chloride and 50 g of THF was added to the diluted reactant with dropping funnel. Thereafter, 10 ml of triethylamine was added to the reactant, and the reactant was refluxed under nitrogen atmosphere for 12 hours. After completion of the reaction, the solvent was removed by vacuum distillation of the reactant. And then, the reactant was separated by a liquid chromatography (silica gel, hexane:ether=6:1), and the solvent was removed again. The reactant, which did not contain solvent, was recrystallized by hexane, and then the recrystallized reactant was stayed at the room temperature to obtain 20.5 g of monomer represented by the following Formula 7a with 77% yield. {$^1$H-NMR(CDCl$_3$): δ(ppm) 6.33(CH, 2H), 6.05(CH, 2H), 5.72(CH, 2H), 1.52(CH$_2$, 2H), 1.38(CH$_2$, 4H), 0.85(CH$_3$, 6H)}.

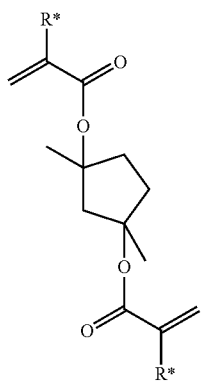

[Formula 7a]

In Formula 7a, R* is a hydrogen.

EXAMPLE 1-2

Preparation of Monomer

A. Preparation of Cyclic Diol of Formula 6b

Except for using 11.2 g(0.1 mol) of cyclohexane-1,4-dione instead of 9.8 g of cyclopentane-1,3-dione, 11.8 g of cyclic diol, represented by the following Formula 6b, was obtained with 82% yield in the same manner as described in Example 1-1-A. {$^1$H-NMR(CDCl$_3$): δ(ppm) 3.51(OH, 2H), 1.29(CH$_2$, 8H), 0.84(CH$_3$, 6H)}

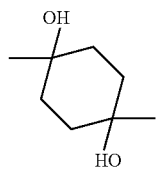

[Formula 6b]

B. Preparation of Monomer of Formula 7b

Except for using 14.4 g(0.1 mol) of cyclic diol of Formula 6b prepared in Example 1-2-A instead of 13.02 g of cyclic diol of Formula 6a prepared in Example 1-1-A, 18.8 g of monomer represented by the following Formula 7b was obtained with 67% yield in the same manner as described in Example 1-1-B. {$^1$H-NMR(CDCl$_3$): δ(ppm) 6.33(CH, 2H), 6.05(CH, 2H) 5.72(CH, 2H), 1.16(CH$_2$, 8H), 0.82(CH$_3$, 6H)}.

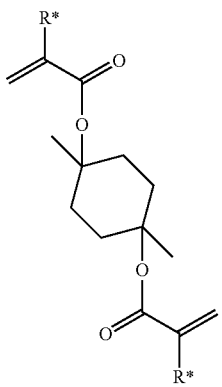

[Formula 7b]

In Formula 7b, R* is a hydrogen.

EXAMPLE 1-3

Preparation of Monomer

A. Preparation of Cyclic Diol of Formula 6c

Except for using 16.6 g(0.1 mol) of 1,5-dimethylbicyclo[3,3,0]octane-3,7-dione instead of 9.8 g of cyclopentane-1,3-dione, 15.4 g of cyclic diol, represented by the following Formula 6c, was obtained with 78% yield in the same manner as described in Example 1-1-A. {$^1$H-NMR(CDCl$_3$): δ(ppm) 3.46(OH, 2H), 1.31(CH$_2$, 8H), 1.12(CH$_3$, 6H), 0.78(CH$_3$, 6H)}.

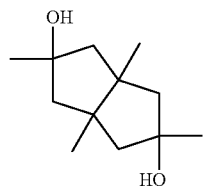

[Formula 6c]

B. Preparation of Monomer of Formula 7c

Except for using 19.8 g(0.1 mol) of cyclic diol of Formula 6c prepared in Example 1-3-A instead of 13.02 g of cyclic diol of Formula 6a prepared in Example 1-1-A, 16.9 g of monomer represented by the following Formula 7c was obtained with 49% yield in the same manner as described in Example 1-1-B. {$^1$H-NMR(CDCl$_3$): δ (ppm) 6.33(CH, 2H), 6.05(CH, 2H), 5.72(CH, 2H), 1.26(CH$_2$, 8H), 1.11(CH$_3$, 6H), 0.77(CH$_3$, 6H)}.

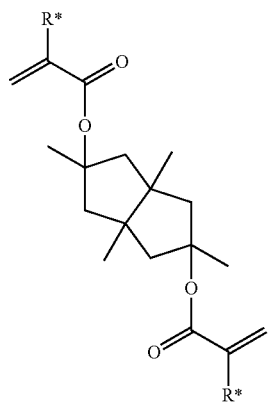

[Formula 7c]

In Formula 7c, R* is a hydrogen.

EXAMPLE 1-4

Preparation of Monomer

A. Preparation of Cyclic Diol of Formula 6d

Except for using 12.4 g(0.1 mol) of 7,7-dimethyl-bicyclo[2,2,1]heptane-2,3-dione instead of 9.8 g of cyclopentane-1, 3-dione, 10.4 g of cyclic diol, represented by the following Formula 6d, was obtained with 67% yield in the same manner as described in Example 1-1-A. {$^1$H-NMR(CDCl$_3$): δ(ppm) 3.53(OH, 2H), 1.61(CH, 2H), 1.45(CH$_2$, 4H), 1.14(CH$_3$, 6H), 0.85(CH$_3$, 6H)}.

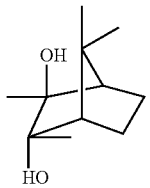

[Formula 6d]

B. Preparation of Monomer of Formula 7d

Except for using 15.6 g(0.1 mol) of cyclic diol of Formula 6d prepared in Example 1-4-A, instead of 13.02 g of cyclic diol of Formula 6a prepared in Example 1-1-A, 17.4 g of monomer represented by the following Formula 7d was obtained with 60% yield in the same manner as described in Example 1-1-B. {$^1$H-NMR(CDCl$_3$): δ(ppm) 6.33(CH, 2H), 6.05(CH, 2H), 5.72(CH, 2H), 1.54(CH, 2H), 1.44(CH$_2$, 4H), 1.13(CH$_3$, 6H), 0.81(CH$_3$, 6H)}.

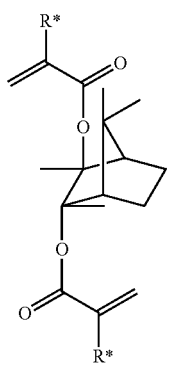

[Formula 7d]

In Formula 7d, R* is a hydrogen.

EXAMPLE 1-5

Preparation of Monomer

A. Preparation of cyclic diol of Formula 6e

Except for using 16.4 g(0.1 mol) of adamantan-2,6-dione instead of 9.8 g of cyclopentane-1,3-dione, 14.8 g of cyclic diol, represented by the following Formula 6e, was obtained with 76% yield in the same manner as described in Example 1-1-A. {$^1$H-NMR(CDCl$_3$): δ(ppm) 3.44(OH, 2H), 1.58(CH, 4H), 1.40(CH$_2$, 4H), 1.29(CH$_2$, 4H), 0.80(CH$_3$, 6H)}

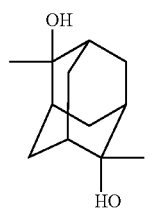

[Formula 6e]

B. Preparation of Monomer of Formula 7e

Except for using 19.6 g(0.1 mol) of cyclic diol of Formula 6e prepared in Example 1-5-A, instead of 13.02 g of cyclic diol of Formula 6a prepared in Example 1-1-A, 18.4 g of monomer represented by the following Formula 7e was obtained with 55% yield in the same manner as described in Example 1-1-B. {$^1$H-NMR(CDCl$_3$): δ(ppm) 6.33(CH, 2H), 6.05(CH, 2H), 5.72(CH, 2H), 1.61 (CH, 4H), 1.44(CH$_2$, 4H), 1.28(CH$_2$, 4H), 0.82(CH$_3$, 6H)}

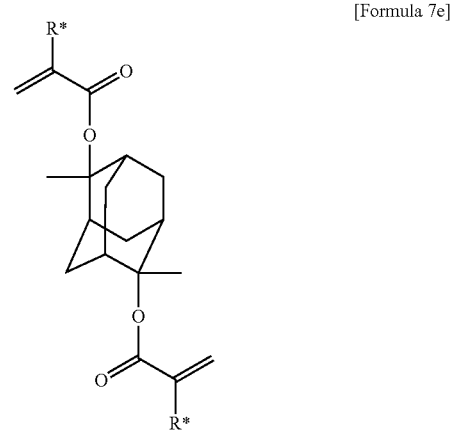

[Formula 7e]

In Formula 7e, R* is a hydrogen.

EXAMPLE 1-6

Preparation of Monomer

A. Preparation of Cyclic Diol of Formula 6f

Except for using 23.6 g(0.1 mol) of 2,2'-bis-4,4'-carbonyl-cyclohexylpropane instead of 9.8 g of cyclopentane-1,3-dione, 23.3 g of cyclic diol, represented by the following Formula 6f, was obtained with 87% yield in the same manner as described in Example 1-1-A. {$^1$H-NMR(CDCl$_3$): δ(ppm) 3.44(OH, 2H), 1.56(CH, 2H), 1.38(CH$_2$, 8H), 1.28(CH$_2$, 8H), 1.19(CH$_3$, 6H), 0.74(CH$_3$, 6H)}.

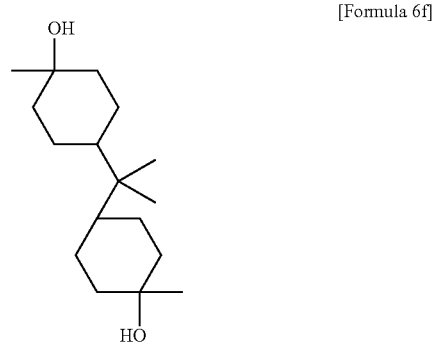

[Formula 6f]

B. Preparation of Monomer of Formula 7f

Except for using 26.8 g(0.1 mol) of cyclic diol of Formula 6f prepared in Example 1-6-A, instead of 13.02 g of cyclic diol of Formula 6a prepared in Example 1-1-A, 23.5 g of monomer represented by the following Formula 7f was obtained with 58% yield in the same manner as described in Example 1-1-B. {$^1$H-NMR(CDCl$_3$): δ(ppm) 6.33(CH, 2H), 6.05(CH, 2H), 5.72(CH, 2H), 1.35(CH$_2$, 8H), 1.27(CH$_2$, 8H), 1.20(CH$_3$, 6H), 0.75(CH$_3$, 6H)}.

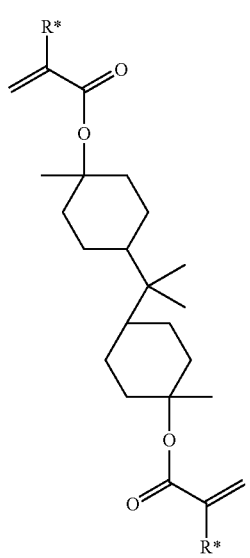

[Formula 7f]

In Formula 7f, R* is a hydrogen.

EXAMPLE 1-7

Preparation of Monomer

A. Preparation of Cyclic Diol of Formula 6g

Except for using 19.4 g(0.1 mol) of 2,2'-bis-4,4'-carbonyl-cyclohexyl instead of 9.8 g of cyclopentane-1,3-dione, 18.5 g of cyclic diol, represented by the following Formula 6g, was obtained with 83% yield in the same manner as described in Example 1-1-A.{$^1$H-NMR(CDCl$_3$): δ(ppm) 3.48(OH, 2H), 1.59(CH, 2H), 1.40(CH$_2$, 8H), 1.27(CH$_2$, 8H), 0.76(CH$_3$, 6H)}.

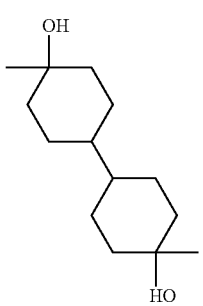

[Formula 6g]

B. Preparation of Monomer of Formula 7g

Except for using 22.6 g(0.1 mol) of cyclic diol of Formula 6g prepared in Example 1-7-A, instead of 13.02 g of cyclic diol of Formula 6a prepared in Example 1-1-A, 17.2 g of monomer represented by the following Formula 7g was obtained with 48% yield in the same manner as described in Example 1-1-B. {$^1$H-NMR(CDCl$_3$): δ(ppm) 6.32(CH, 2H), 6.04(CH, 2H), 5.70(CH, 2H), 1.56(CH, 2H), 1.37(CH$_2$, 8H), 1.24(CH$_2$, 8H), 0.74(CH$_3$, 6H)}.

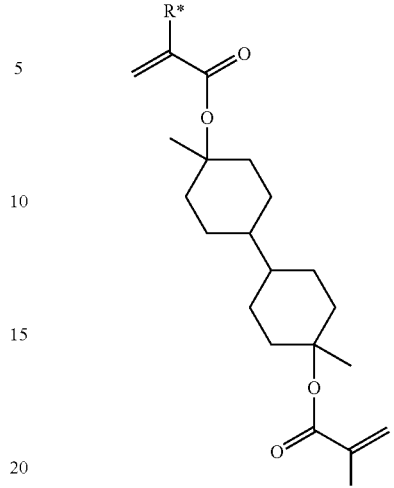

[Formula 7g]

In Formula 7g, R* is a hydrogen.

EXAMPLE 1-8

Preparation of Monomer of Formula 8a

After refluxing nitrogen in 500 ml 3 necks round-bottom flask, 100.0 g(0.3 mol) of 3.0M-methyl magnesium bromide was added into the flask, and then the reactor was cooled to the temperature of 0° C. Thereafter, a solution of 9.8 g(0.1 mol) of cyclopentane-1,3-dione dissolved in 100 g of THF was dropped into the reactor with dropping funnel for 30 minutes, and then the reactor was heated to room temperature and stirred for 2 hours. After cooling the reactor to the temperature of 0° C., a mixture solution of 18.2 g of acryloyl chloride and 50 g of THF was dropped into the reactor with dropping funnel slowly for 1 hour. Thereafter, the reaction mixture was stirred at the temperature of 0° C. for 2 hours, and then stayed at the room temperature, and stirred for 24 hours. In order to complete the reaction, 100 ml of cold water was added to the reactant. Thereafter, the reactant was placed in saparatory funnel, and extracted with diethylether for 3 times. And then, the extract was purified by a column chromatography(hexane:ethylacetate=4:1) to obtain 18.1 g of monomer represented by the following Formula 8a, with 68% yield. {$^1$H-NMR(CDCl$_3$): δ(ppm) 6.33(CH, 2H), 6.05(CH, 2H) 5.72(CH, 2H), 1.52(CH$_2$, 2H), 1.38(CH$_2$, 4H), 0.85(CH$_3$, 6H)}.

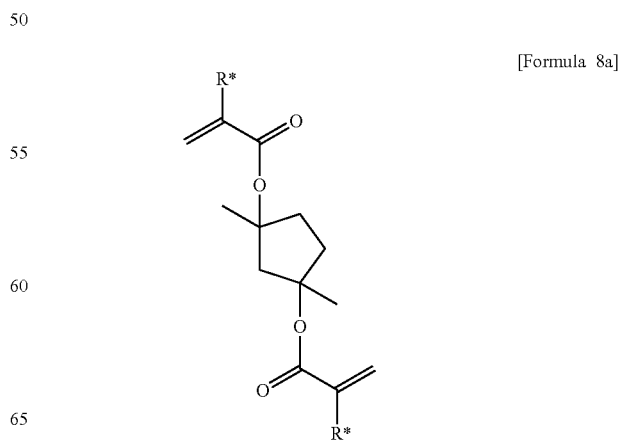

[Formula 8a]

In Formula 8a, R* is a hydrogen.

EXAMPLE 1-9

Preparation of Monomer of Formula 8b

Except for using 11.2 g of cyclohexane-1,4-dione(0.1 mol) instead of 9.8 g of cyclopentane-1,3-dione, 20.2 g of monomer, represented by the following Formula 8b, was obtained with 72% yield in the same manner as described in Example 1-8. {$^1$H-NMR(CDCl$_3$): δ(ppm) 6.33(CH, 2H), 6.05(CH, 2H), 5.72(CH, 2H), 1.16(CH$_2$, 8H), 0.82(CH$_3$, 6H)}.

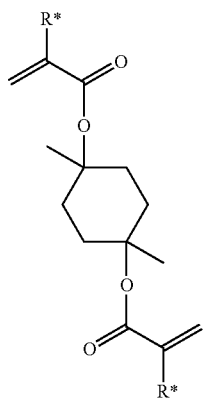

[Formula 8b]

In Formula 8b, R* is a hydrogen.

EXAMPLE 1-10

Preparation of Monomer of Formula 8c

Except for using 16.6 g of 1,5-dimethyl-bicyclo[3,3,0]octane-3,7-dione (0.1 mol) instead of 9.8 g of cyclopentane-1,3-dione, 21.7 g of monomer, represented by the following Formula 8c, was obtained with 65% yield in the same manner as described in Example 1-8. {$^1$H-NMR(CDCl$_3$): δ(ppm) 6.33(CH, 2H), 6.05(CH, 2H), 5.72(CH, 2H), 1.26(CH$_2$, 8H), 1.11(CH$_3$, 6H), 0.77(CH$_3$, 6H)}.

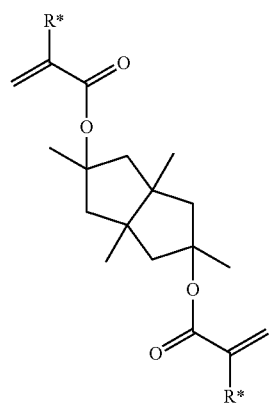

[Formula 8c]

In Formula 8c, R* is a hydrogen.

EXAMPLE 1-11

Preparation of Monomer of Formula 8d

Except for using 15.2 g of 7,7-dimethyl-nobornane-2,3-dione(0.1 mol) instead of 9.8 g of cyclopentane-1,3-dione, 15.2 g of monomer, represented by the following Formula 8d, was obtained with 52% yield in the same manner as described in Example 1-8. {$^1$H-NMR(CDCl$_3$): δ(ppm) 6.33(CH, 2H), 6.05(CH, 2H), 5.72(CH, 2H), 1.54(CH, 2H), 1.44(CH$_2$, 4H), 1.13(CH$_3$, 6H), 0.81(CH$_3$, 6H)}.

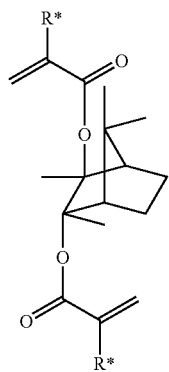

[Formula 8d]

In Formula 8d, R* is a hydrogen.

EXAMPLE 1-12

Preparation of Monomer of Formula 8e

Except for using 16.4 g of adamantane-2,6-dione(0.1 mol) instead of 9.8 g of cyclopentane-1,3-dione, 19.6 g of monomer, represented by the following Formula 8e, was obtained with 59% yield in the same manner as described in Example 1-8. {$^1$H-NMR(CDCl$_3$): δ(ppm) 6.33(CH, 2H), 6.05(CH, 2H), 5.72(CH, 2H), 1.61 (CH, 4H), 1.44(CH$_2$, 4H), 1.28 (CH$_2$, 4H), 0.82(CH$_3$, 6H)}

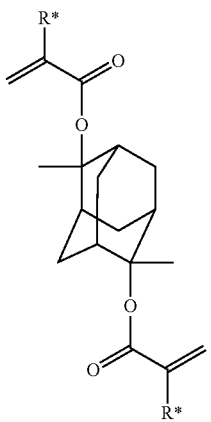

[Formula 8e]

In Formula 8e, R* is a hydrogen.

EXAMPLE 1-13

Preparation of Monomer of Formula 8f

Except for using 23.6 g of 2,2'-bis-4,4'-carbonylcyclohexylpropane(0.1 mol) instead of 9.8 g of cyclopentane-1,3-dione, 19.8 g of monomer, represented by the following Formula 8f, was obtained with 49% yield in the same manner as described in Example 1-8. {$^1$H-NMR(CDCl$_3$): δ(ppm) 6.33 (CH, 2H), 6.05(CH, 2H), 5.72(CH, 2H), 1.35(CH$_2$, 8H), 1.27 (CH$_2$, 8H), 1.20(CH$_3$, 6H), 0.75(CH$_3$, 6H)}.

[Formula 8f]

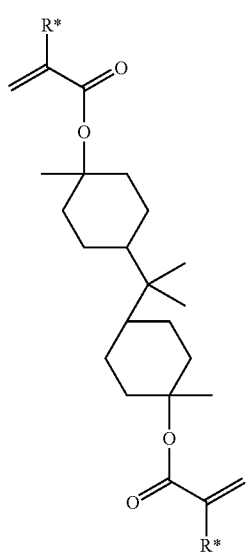

In Formula 8f, R* is a hydrogen.

EXAMPLE 1-14

Preparation of Monomer of Formula 8g

Except for using 19.4 g of 2,2'-bis-4,4'-carbonylcyclohexyl (0.1 mol) instead of 9.8 g of cyclopentane-1,3-dione, 19.6 g of monomer, represented by the following Formula 8g, was obtained with 54% yield in the same manner as described in Example 1-8. {$^1$H-NMR(CDCl$_3$): δ(ppm) 6.32(CH, 2H), 6.04(CH, 2H) 5.70(CH, 2H), 1.56(CH, 2H), 1.37(CH$_2$, 8H), 1.24(CH$_2$, 8H), 0.74(CH$_3$, 6H)}.

[Formula 8g]

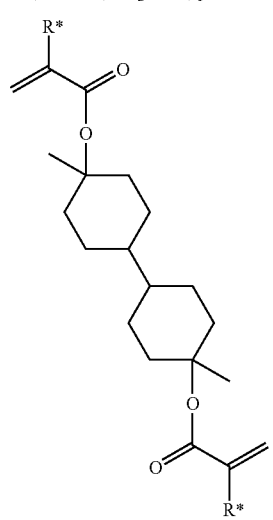

In Formula 8g, R* is a hydrogen.

EXAMPLE 2-1

Preparation of Polymer of Formula 3a 26.6 g(0.1 mol) of the monomer represented by Formula 7a, 14.3 g(0.05 mol) of 2-methyl-2-adamantyl-5-nobornyl-2-carboxylate, 4.9 g(0.05 mol) of maleic anhydride, 22.2 g (0.1 mol) of 2-methyl-2-adamantyl methacrylate and 0.7 g of azobis(isobutyronitrile)(AlBN) were added into a reactor, and the reactant was dissolved in 25 g of THF. Subsequently, the gas in the reactor was removed by a freezing method with an ampoule, and the polymerization was carried out at 68° C. for 24 hours. After completion of the polymerization reaction, the reactant was slowly dropped to a lot of diethylether and was precipitated in diethylehter. Then, the precipitant was dissolved in THF again, and the dissolved reactant was reprecipitated in diethylether to obtain 42.8 g of the polymer represented by Formula 3a with 62% yield (GPC(Gel Permeation Chromatography) analysis, Mn(=number average molecular weight): 5,326, Mw(=weight average molecular weight): 9,312, PD(=polydispersity): 1.75).

EXAMPLE 2-2

Preparation of Polymer of Formula 3b

Except for using 28.0 g(0.1 mol) of the monomer represented by Formula 7b, 14.3 g(0.05 mol) of 2-methyl-2-adamantyl-5-nobornyl-2-carboxylate, 4.9 g(0.05 mol) of maleic anhydride and 22.2 g(0.1 mol) of 2-methyl-2-adamantyl methacrylate, 46.8 g of the polymer represented by Formula 3b was obtained with 67% yield in the same manner as described in Example 2-1 (Mn: 5,024, Mw: 8,958, PD: 1.78).

EXAMPLE 2-3

Preparation of Polymer of Formula 3c

Except for using 33.4 g(0.1 mol) of the monomer represented by Formula 7c, 14.3 g(0.05 mol) of 2-methyl-2-adamantyl-5-nobornyl-2-carboxylate, 4.9 g(0.05 mol) of maleic anhydride and 22.2 g (0.1 mol) of 2-methyl-2-adamantyl methacrylate, 41.1 g of the polymer represented by Formula 3c was obtained with 55% yield in the same manner as described in Example 2-1 (Mn: 5,135, Mw: 9,626, PD: 1.87).

EXAMPLE 2-4

Preparation of Polymer of Formula 3d

Except for using 29.2 g(0.1 mol) of the monomer represented by Formula 7d, 14.3 g(0.05 mol) of 2-methyl-2-adamantyl-5-nobornyl-2-carboxylate, 4.9 g(0.05 mol) of maleic anhydride and 22.2 g (0.1 mol) of 2-methyl-2-adamantyl methacrylate, 40.8 g of the polymer represented by Formula 3d was obtained with 57% yield in the same manner as described in Example 2-1 (Mn: 4,687, Mw: 8,679, PD: 1.85).

EXAMPLE 2-5

Preparation of Polymer of Formula 3e

Except for using 33.2 g(0.1 mol) of the monomer represented by Formula 7e, 14.3 g(0.05 mol) of 2-methyl-2-adamantyl-5-nobornyl-2-carboxylate, 4.9 g(0.05 mol) of maleic anhydride and 22.2 g(0.1 mol) of 2-methyl-2-adamantyl methacrylate, 48.5 g of the polymer represented by Formula 3e was obtained with 65% yield in the same manner as described in Example 2-1 (Mn: 5,621, Mw: 10,240, PD: 1.82).

EXAMPLE 2-6

Preparation of Polymer of Formula 3f

Except for using 40.4 g(0.1 mol) of the monomer represented by Formula 7f, 14.3 g(0.05 mol) of 2-methyl-2-adamantyl-5-nobornyl-2-carboxylate, 4.9 g(0.05 mol) of maleic anhydride and 22.2 g(0.1 mol) of 2-methyl-2-adamantyl methacrylate, 51.0 g of the polymer represented by Formula 3f was obtained with 62% yield in the same manner as described in Example 2-1 (Mn: 4,793, Mw: 9,103, PD: 1.90).

EXAMPLE 2-7

Preparation of Polymer of Formula 3g

Except for using 36.2 g(0.1 mol) of the monomer represented by Formula 7g, 14.3 g(0.05 mol) of 2-methyl-2-adamantyl-5-nobornyl-2-carboxylate, 4.9 g(0.05 mol) of maleic anhydride and 22.2 g(0.1 mol) of 2-methyl-2-adamantyl methacrylate, 44.1 g of the polymer represented by Formula 3 g was obtained with 56% yield in the same manner as described in Example 2-1 (Mn: 4,933, Mw: 9,213, PD: 1.87).

EXAMPLE 2-8

Preparation of Polymer of Formula 5a 26.6 g(0.1 mol) of the monomer represented by Formula 8a, 11.8 g(0.05 mol) of 9-methacryloyloxy-4-oxa-tricyclo[5,2,1,0$^{2,6}$]decane-3-one, 22.2 g(0.1 mol) of 2-methyl-2-adamantyl methacrylate, 11.8 g(0.05 mol) of 1-methacryloyl oxy-3-hydroxy adamantane and 0.7 g of azobisisobutyronitrile(AlBN) were added into a reactor, and the reactant was dissolved in 25 g of THF. Subsequently, the gas in the reactor was removed by a freezing method with an ampoule, and the polymerization was carried out at 68° C. for 24 hours. After completion of the polymerization reaction, the reactant was slowly dropped to a lot of diethylether and was precipitated in diethylehter. Then, the precipitant was dissolved in THF again, and the dissolved reactant was reprecipitated in diethylether to obtain 54.3 g of the polymer represented by Formula 5a with 75% yield(Mn: 5,231, Mw: 9,520, PD: 1.82).

EXAMPLE 2-9

Preparation of Polymer of Formula 5b

Except for using 28.0 g(0.1 mol) of the monomer represented by Formula 8b, 11.8 g(0.05 mol) of 9-methacryloyloxy-4-oxa-tricyclo[5,2,1,0$^{2,6}$]decane-3-one, 22.2 g(0.1 mol) of 2-methyl-2-adamantyl methacrylate, 11.8 g(0.05 mol) of 1-methacryloyl oxy-3-hydroxy adamantane, 52.4 g of the polymer represented by Formula 5b was obtained with 71% yield in the same manner as described in Example 2-8(Mn: 4,885, Mw: 8,745, PD: 1.79).

EXAMPLE 2-10

Preparation of Polymer of Formula 5c

Except for using 33.4 g(0.1 mol) of the monomer represented by Formula 8b, 11.8 g(0.05 mol) of 9-methacryloyloxy-4-oxa-tricyclo[5,2,1,0$^{2,6}$]decane-3-one, 22.2 g(0.1 mol) of 2-methyl-2-adamantyl methacrylate, 11.8 g(0.05 mol) of 1-methacryloyl oxy-3-hydroxy adamantane, 53.9 g of the polymer represented by Formula 5c was obtained with 68% yield in the same manner as described in Example 2-8(Mn: 5,728, Mw: 9,681, PD: 1.69).

EXAMPLE 2-11

Preparation of Polymer of Formula 5d

Except for using 29.2 g(0.1 mol) of the monomer represented by Formula 8d, 11.8 g(0.05 mol) of 9-methacryloyloxy-4-oxa-tricyclo[5,2,1,0$^{2,6}$]decane-3-one, 22.2 g(0.1 mol) of 2-methyl-2-adamantyl methacrylate, 11.8 g(0.05 mol) of 1-methacryloyl oxy-3-hydroxy adamantane, 55.5 g of the polymer represented by Formula 5d was obtained with 74% yield in the same manner as described in Example 2-8(Mn: 4,432, Mw: 8,287, PD: 1.87).

EXAMPLE 2-12

Preparation of Polymer of Formula 5e

Except for using 33.2 g(0.1 mol) of the monomer represented by Formula 8e, 11.8 g(0.05 mol) of 9-methacryloyloxy-4-oxa-tricyclo[5,2,1,0$^{2,6}$]decane-3-one, 22.2 g (0.1 mol) of 2-methyl-2-adamantyl methacrylate, 11.8 g (0.05 mol) of 1-methacryloyl oxy-3-hydroxy adamantane, 49.8 g of the polymer represented by Formula 5e was obtained with 63% yield in the same manner as described in Example 2-8 (Mn: 5,218, Mw: 9,967, PD: 1.91).

EXAMPLE 2-13

Preparation of Polymer of Formula 5f

Except for using 40.4 g(0.1 mol) of the monomer represented by Formula 8f, 11.8 g(0.05 mol) of 9-methacryloyloxy-4-oxa-tricyclo[5,2,1,0$^{2,6}$]decane-3-one, 22.2 g(0.1 mol) of 2-methyl-2-adamantyl methacrylate, 11.8 g(0.05 mol) of 1-methacryloyl oxy-3-hydroxy adamantane, 53.4 g of the polymer represented by Formula 5f was obtained with 62% yield in the same manner as described in Example 2-8(Mn: 5,967, Mw: 10,024, PD: 1.68).

EXAMPLE 2-14

Preparation of Polymer of Formula 5g

Except for using 36.2 g(0.1 mol) of the monomer represented by Formula 8g, 11.8 g(0.05 mol) of 9-methacryloyloxy-4-oxa-tricyclo[5,2,1,0$^{2,6}$]decane-3-one, 22.2 g(0.1 mol) of 2-methyl-2-adamantyl methacrylate, 11.8 g(0.05 mol) of 1-methacryloyl oxy-3-hydroxy adamantane, 57.4 g of the polymer represented by Formula 5g was obtained with 70% yield in the same manner as described in Example 2-8(Mn: 5,324, Mw: 9,158, PD: 1.72).

EXAMPLES 3-1 TO 3-14

Preparation of Photoresist Composition 2 g of polymer obtained in Example 2-1, 0.024 g of phthalimido trifluoromethane sulfonate and 0.06 g of triphenylsulfonium triflate were dissolved in 20 g of propyleneglycol-monomethyletheracetate(PGMEA), and then a photoresist composition was prepared by filtering the mixture with a filter of 0.20 μm pore size(Example 3-1).

Except for using 2 g of polymer prepared in Example 2-2 to 2-14 instead of 2 g of polymer prepared in Example 2-1, photoresist compositions were prepared in the same manner as described in Example 3-1 (Examples 3-2 to 3-14).

EXAMPLES 4-1 TO 4-14

Formation of Photoresist Pattern

Figure 2:
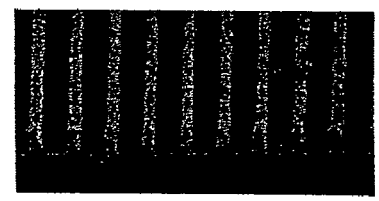
Figure 3:
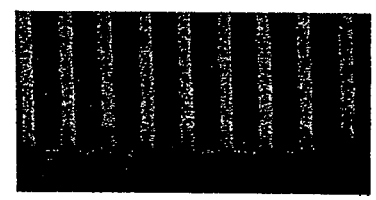
Figure 4:
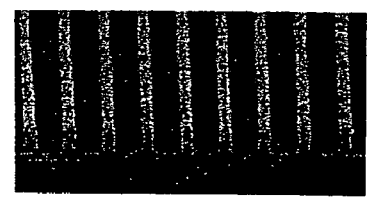
Figure 5:
Figure 6:
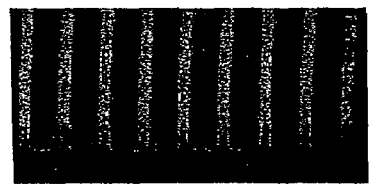
Figure 7:
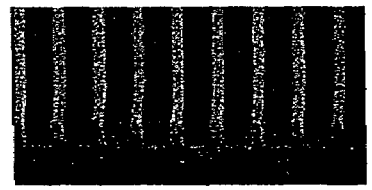
Figure 8:
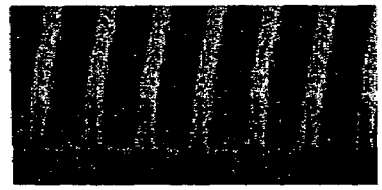
Figure 9:
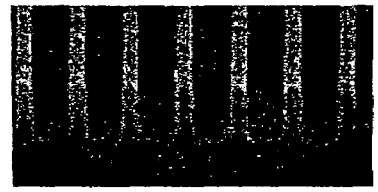
Figure 10:
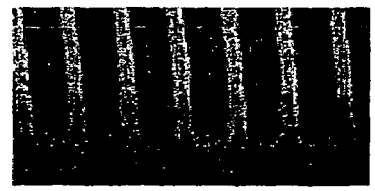
Figure 11:
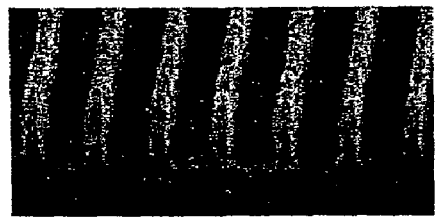
Figure 12:
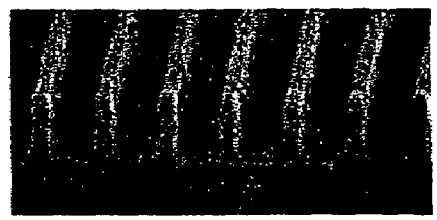
Figure 13:
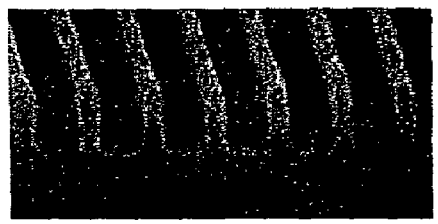
Figure 14:
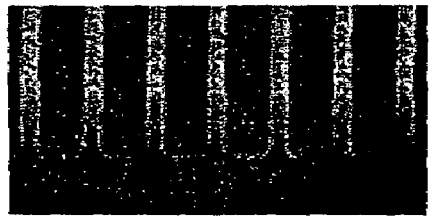

The photoresist compositions prepared in Examples 3-1 to 3-14 were spin coated on the upper parts of silicon wafers to prepare thin-films of photoresist. The photoresist layer was pre-baked at a temperature of 90° C. for 90 seconds in an oven or on a hot plate, and was exposed with an ArF excimer laser, and was post-baked at a temperature of 120° C. for 90 seconds. Thereafter, the baked wafer was developed with 2.38 weight % of TMAH solution for about 40 seconds, thereby forming a 0.07 μm line/space patterns. The properties of the produced photoresist patterns were shown in Table 1, SEM (Scanning Electron Microscopy) photographs of the photoresist patterns which were formed with the photoresist compositions of Examples 3-1 to 3-14 were shown in FIGS. 1 to 14.

TABLE 1

| Resist composition | Minimum resolution [μm] | Focus depth [μm] | Line Edge Roughness [nm] | Energy process margin [%] | Post exposure bake sensitivity [nm/° C.] | Dry etching resistance |
|---|---|---|---|---|---|---|
| Example 3-1 | 0.065 | 0.40 | 5.8 | 13.4 | 2.5 | Very good |
| Example 3-2 | 0.065 | 0.30 | 4.9 | 12.8 | 3.0 | Very good |
| Example 3-3 | 0.065 | 0.35 | 4.2 | 16.1 | 1.5 | Very good |
| Example 3-4 | 0.065 | 0.45 | 6.1 | 15.6 | 1.5 | Good |
| Example 3-5 | 0.065 | 0.45 | 4.9 | 11.3 | 2.5 | Good |
| Example 3-6 | 0.065 | 0.35 | 5.3 | 12.3 | 1.0 | Very good |
| Example 3-7 | 0.065 | 0.40 | 4.5 | 12.3 | 2.0 | Good |
| Example 3-8 | 0.065 | 0.35 | 5.5 | 11.6 | 1.5 | Very good |
| Example 3-9 | 0.065 | 0.35 | 6.2 | 13.8 | 2.0 | Very good |
| Example 3-10 | 0.065 | 0.30 | 4.2 | 12.6 | 2.0 | Good |
| Example 3-11 | 0.065 | 0.40 | 5.1 | 15.4 | 1.5 | Very good |
| Example 3-12 | 0.065 | 0.45 | 4.8 | 16.1 | 3.0 | Good |
| Example 3-13 | 0.065 | 0.35 | 5.9 | 14.5 | 2.5 | Good |
| Example 3-14 | 0.065 | 0.45 | 5.6 | 16.3 | 1.5 | Very good |

The photoresist monomer having alcohol ester groups, a polymer thereof and a photoresist composition including the same according to the present invention can improve the resolution and the process margin due to the low activation energy of the deprotection reaction of the alcohol ester group, and also can produce fine photoresist patterns because they have a high dry etching resistance and stable PEB(Post Exposure Baking) temperature sensitivity. Further, the polymers thereof and photoresist compositions including the same can improve the focus depth margin and the line edge roughness of the resist layer. The photoresist polymer according to the present invention is formed only by (meth)acrylate linkages, and thus, the next etching process can be easily performed even if the coating thickness of the polymer is low, for example, is less than 2000 Å. Therefore, the polymer can be used in the lithography process using an extreme short wavelength light source and an electron beam, and the polymerization yield highly increases compared with the conventional hybrid-type polymer. And also, the selectivity of the light exposed area to the light non-exposed area can be improved due to the partially crosslinked structure. While the present invention has been described in detail with reference to the preferred embodiments, those skilled in the art will appreciate that various modifications and substitutions can be made thereto without departing from the spirit and scope of the present invention as set for the in the appended claims.

What is claimed is:

1. A monomer represented by the following Formula 1,

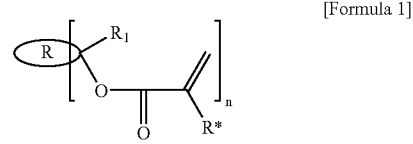

[Formula 1]

wherein, R* is a hydrogen or methyl group, $R_1$ is saturated hydrocarbyl group of 1 to 5 carbon atoms, R is monocyclic or multi-cyclic homo or hetero saturated hydrocarbyl group of 3 to 50 carbon atoms, and n is an integer of at least 2.

2. The monomer according to claim 1, wherein R is selected from the group consisting of

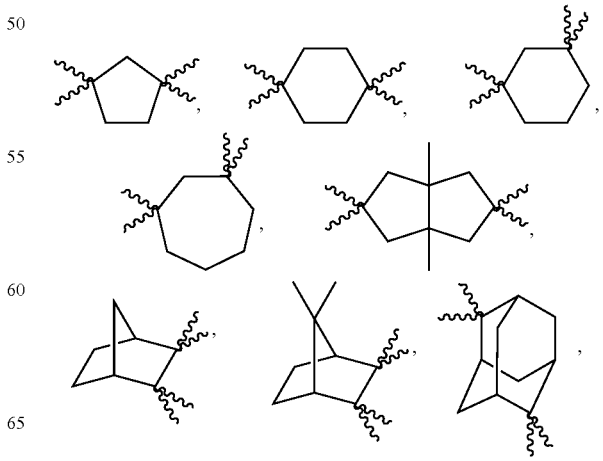

-continued

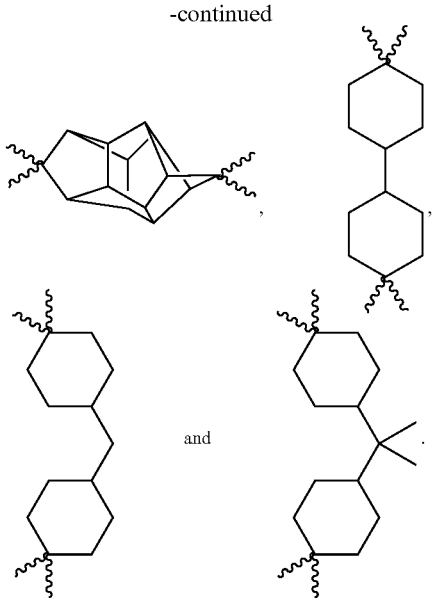

3. The monomer according to claim 1, wherein the monomer is prepared by the alkylmagnesium reaction of cyclic compound having at least 2 ketone groups.

4. A photoresist polymer including a repeating unit represented by the following Formula 2,

[Formula 2]

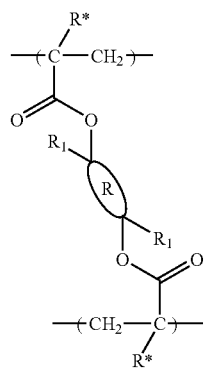

wherein, R* is a hydrogen or methyl group, $R_1$ is saturated hydrocarbyl group of 1 to 5 carbon atoms, R is mono-cyclic or multi-cyclic homo or hetero saturated hydrocarbyl group of 3 to 50 carbon atoms.

5. The photoresist polymer according to claim 4, wherein the photoresist polymer is represented by the following Formula 3,

[Formula 3]

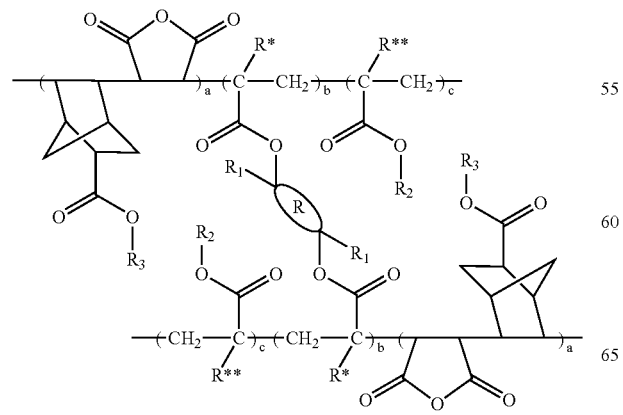

wherein, R*, R** are independently hydrogen or methyl group, $R_1$ is saturated hydrocarbyl group of 1 to 5 carbon atoms, $R_2$, $R_3$ are a chain type or ring type alkyl group of 1 to 20 carbon atoms, R is mono-cyclic or multi-cyclic homo or hetero saturated hydrocarbyl group, a, b and c are mole % of the repeating units composing the upper and lower polymer chains, and are independently 1-95 mole %.

6. The photoresist polymer according to claim 4, wherein the photoresist polymer is selected from the group consisting of polymers of the following Formulas 3a to 3g,

[Formula 3a]

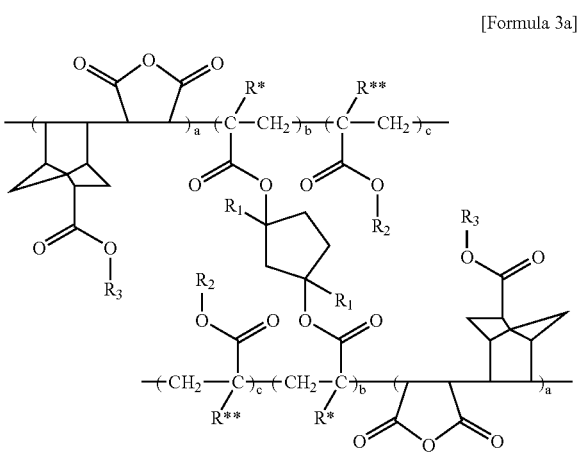

[Formula 3b]

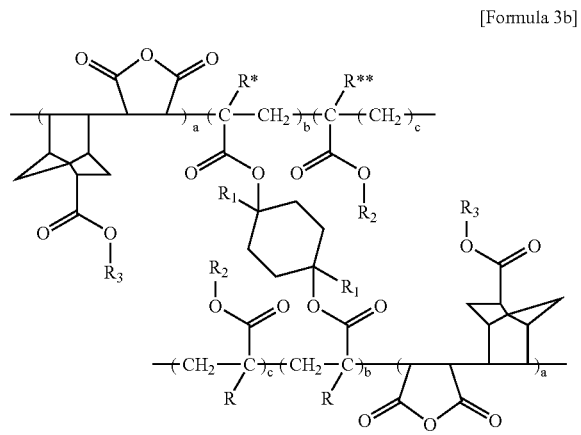

-continued

[Formula 3c]

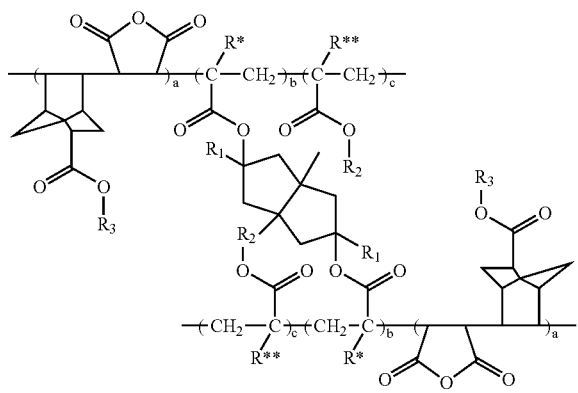

[Formula 3d]

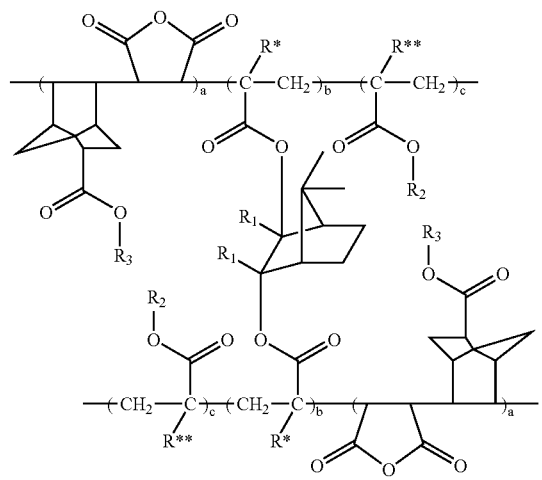

[Formula 3e]

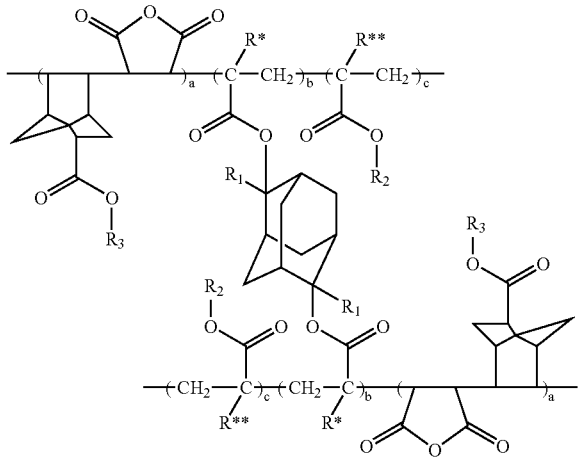

-continued

[Formula 3f]

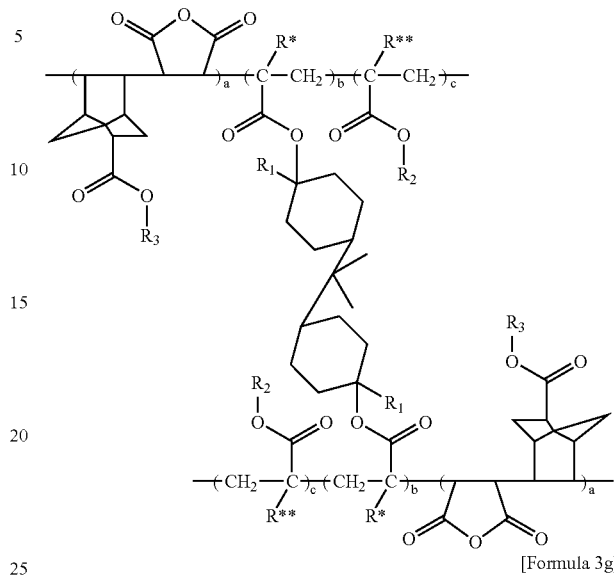

[Formula 3g]

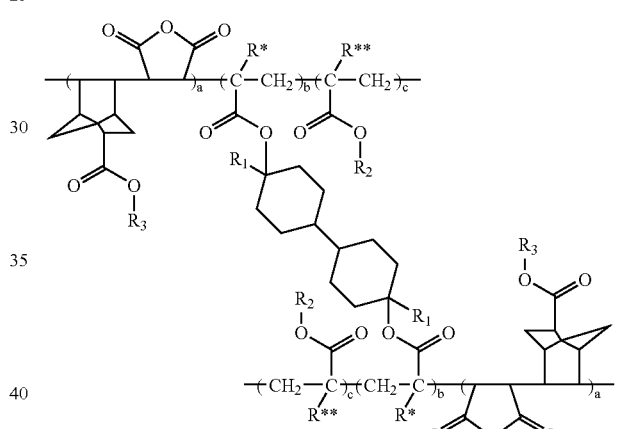

wherein, R*, R** are independently hydrogen or methyl group, $R_1$ is saturated hydrocarbyl group of 1 to 5 carbon atoms, $R_2$, $R_3$ are a chain type or ring type alkyl group of 1 to 20 carbon atoms, R is mono-cyclic or multi-cyclic homo or hetero saturated hydrocarbyl group, a, b and c are mole % of the repeating units composing the upper and lower polymer chains, and are independently 1-95 mole %.

7. A photoresist polymer including a repeating unit represented by the following Formula 4,

[Formula 4]

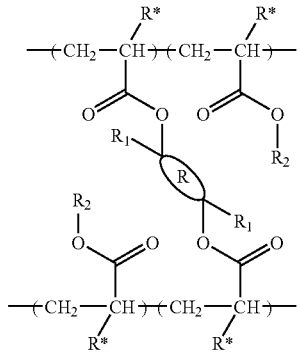

wherein, R* is a hydrogen or methyl group, R₁ is saturated hydrocarbyl group of 1 to 5 carbon atoms, R is mono-cyclic or multi-cyclic homo or hetero saturated hydrocarbyl group of 3 to 50 carbon atoms, and R₂ is a chain type or ring type alkyl group of 1 to 20 carbon atoms.

8. The photoresist polymer according to claim 7, wherein as a repeating monomer in the polymer of Formula 4, (meth)acrylate crosslinking monomer having alcohol ester groups including saturated cyclic hydrocarbyl group is prepared by the one-step reaction of (meth)acryloyl chloride, alkylmagnesium, and cyclic ketone compound having at least 2 ketone groups.

9. The photoresist polymer according to claim 7, wherein the photoresist polymer is represented by the following Formula 5,

[Formula 5]

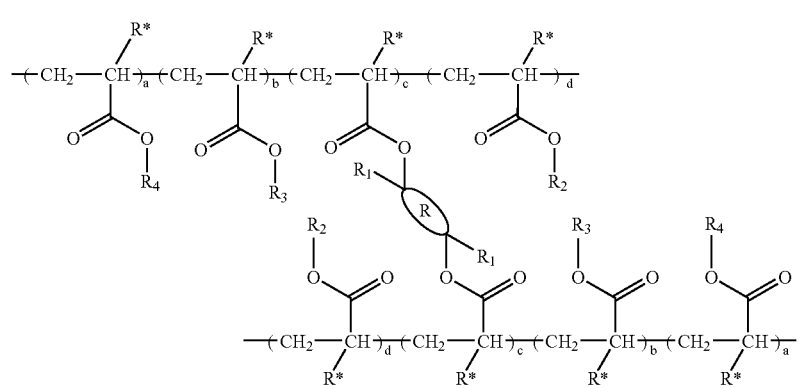

wherein, R* is independently a hydrogen or methyl group, R₁ is saturated hydrocarbyl group of 1 to 5 carbon atoms, R₂, R₃ and R₄ are a chain type or ring type alkyl group of 1 to 20 carbon atoms, R is mono-cyclic or multi-cyclic homo or hetero saturated hydrocarbyl group of 3 to 50 carbon atoms, and a, b, c and d are mole % of the repeating units composing the upper and lower polymer chains, and are independently 1-95 mole %.

10. The photoresist polymer according to claim 9, wherein the photoresist polymer is selected from the group consisting of polymers of the following Formulas 5a to 5g,

[Formula 5a]

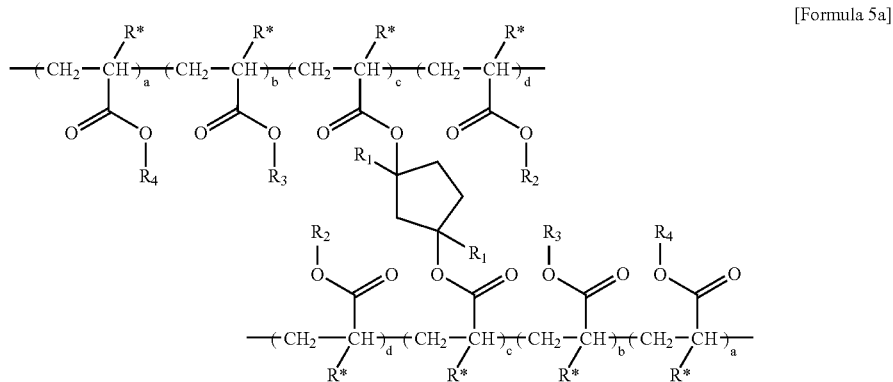

-continued
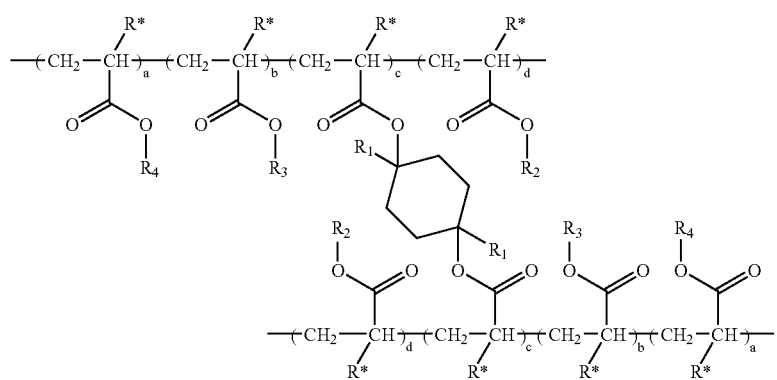
[Formula 5b]
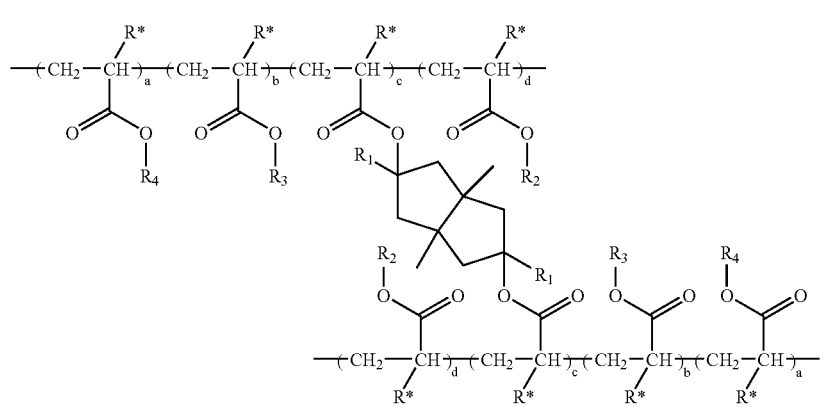
[Formula 5c]
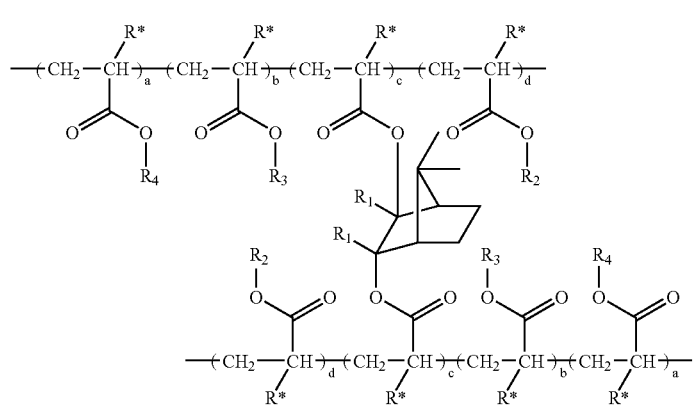
[Formula 5d]
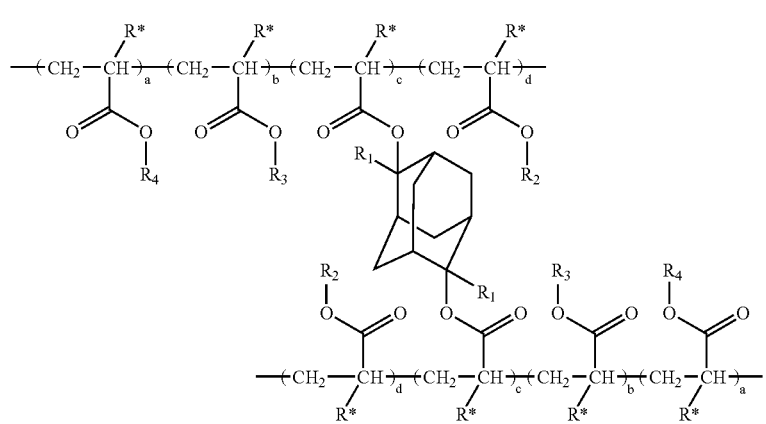
[Formula 5e]

-continued

[Formula 5f]

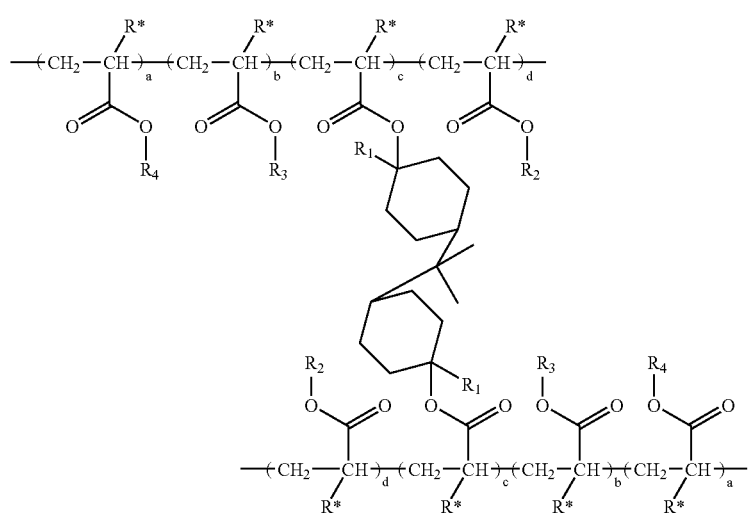

[Formula 5g]

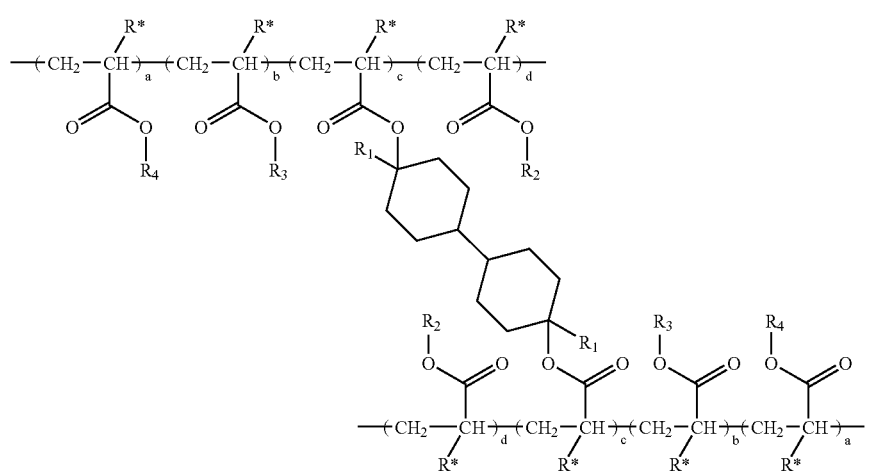

wherein, R*, $R_1$, $R_2$, $R_3$, $R_4$, a, b, c and d are as defined in Formula 5.

11. A photoresist composition comprising:

a photoresist polymer including the repeating unit of the following Formula 2 or 4;

[Formula 2]

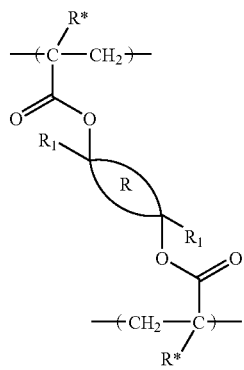

wherein, R* is a hydrogen or methyl group, $R_1$ is saturated hydrocarbyl group of 1 to 5 carbon atoms, R is mono- cyclic or multi-cyclic homo or hetero saturated hydrocarbyl group of 3 to 50 carbon atoms,

[Formula 4]

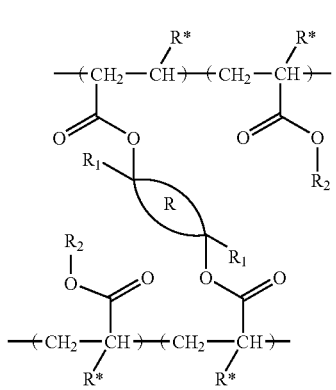

wherein, R* is a hydrogen or methyl group, $R_1$ is saturated hydrocarbyl group of 1 to 5 carbon atoms, R is monocyclic or multi-cyclic homo or hetero saturated hydrocarbyl group of 3 to 50 carbon atoms, and $R_2$ is a chain type or ring type alkyl group of 1 to 20 carbon atoms;

a photo-acid generator for generating a photo-acid; and
an organic solvent.

12. The photoresist composition according to claim 11, wherein the amount of the photoresist polymer is 1 to 30 weight % with respect to the total photoresist composition, and the amount of the photo-acid generator is 0.05 to 10 weight % with respect to the photoresist polymer.

13. The photoresist composition according to claim 11, wherein the photo-acid generator is selected from the group consisting of phthalimidofluoromethane sulfonate, dinitrobenzyltosylate, n-decyl disulfone, naphtylimido trifluoromethan sulfonate, diphenyliodonium hexafluorophosphate, diphenyliodonium hexafluoroarsenate, diphenyliodonium hexafluoroantimonate, diphenyl-p-methoxyphenylsulfonium triflate, diphenyl-p-toluenylsulfonium triflate, diphenyl-p-isobutylphenylsulfonium triflate, triphenylsulfonium hexafluoro arsenate, triphenylsulfonium hexafluoro antimonate, triphenylsulfonium triflate, dibutyinaphtylsulfonium triflate, and the mixtures thereof.

14. The photoresist composition according to claim 11, wherein the organic solvent is selected from the group consisting of ethyleneglycol monomethylether, ethyleneglycol monoethylether, ethyleneglycol monoacetate, diethyleneglycol, diethyleneglycol monoethylether, propyleneglycol monomethyletheracetate, propyleneglycol, propyleneglycol monoacetate, toluene, xylene, methylethylketone, methylisoamylketone, cyclohexanone, dioxane, methyl lactate, ethyl lactate, methylpyruvate, ethylpyruvate, methylmethoxy propionate, ethylethoxy propionate, N,N-dimethylformamide, N,N-dimethylacetamide, N-methyl-2-pyrollidone, 3-ethoxyethylpropionate, 2-heptanone, gamma-butyrolactone, ethyl 2-hydroxypropionate, ethyl 2-hydroxy-2-methyl propionate, ethoxyethyl acetate, hydroxylethyl acetate, methyl 2-hydroxy-3-methylbutanoate, methyl 3-methoxy-2-methylpropionate, ethyl 3-ethoxypropionate, ethyl 3-methoxy-2-methylpropionate, ethyl acetate, butyl acetate, and the mixtures thereof.

15. A method of forming a photoresist pattern comprising the steps of:
forming a photoresist layer by applying the photoresist composition including a photoresist polymer including the repeating unit of the following Formula 2 or 4; a photo-acid generator for producing an acid component; and an organic solvent on a substrate;

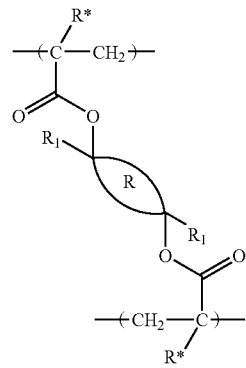

[Formula 2]

wherein, R* is a hydrogen or methyl group, $R_1$ is saturated hydrocarbyl group of 1 to 5 carbon atoms, R is monocyclic or multi-cyclic homo or hetero saturated hydrocarbyl group of 3 to 50 carbon atoms,

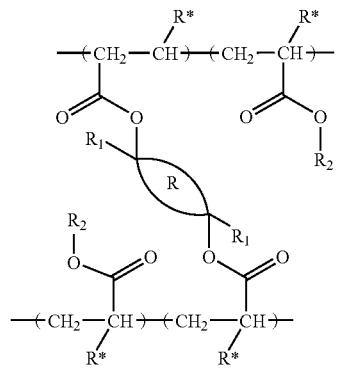

[Formula 4]

wherein, R* is a hydrogen or methyl group, $R_1$ is saturated hydrocarbyl group of 1 to 5 carbon atoms, R is monocyclic or multi-cyclic homo or hetero saturated hydrocarbyl group of 3 to 50 carbon atoms, and $R_2$ is a chain type or ring type alkyl group of 1 to 20 carbon atoms;
forming a predetermined photoresist pattern by exposing the photoresist layer to a light source; and
heating and developing the photoresist pattern.

* * * * *